US 8,243,285 B2

(12) United States Patent
Fishbaine

(10) Patent No.: US 8,243,285 B2
(45) Date of Patent: Aug. 14, 2012

(54) INSPECTION SYSTEM AND METHOD

(76) Inventor: David Fishbaine, Minnetonka, MN (US)

( * ) Notice: Subject to any disclaimer, the term of this patent is extended or adjusted under 35 U.S.C. 154(b) by 0 days.

(21) Appl. No.: 12/567,224

(22) Filed: Sep. 25, 2009

(65) Prior Publication Data
US 2010/0007896 A1  Jan. 14, 2010

Related U.S. Application Data

(63) Continuation of application No. PCT/US2008/059031, filed on Apr. 1, 2008.

(60) Provisional application No. 60/909,862, filed on Apr. 3, 2007.

(51) Int. Cl.
G01B 11/25 (2006.01)
G02B 26/00 (2006.01)

(52) U.S. Cl. ............... 356/603; 359/290; 359/291

(58) Field of Classification Search .......... 356/603–624, 356/445–448, 237.1–237.5; 359/290, 291, 359/224; 382/152, 286; 250/201.9, 492.2
See application file for complete search history.

(56) References Cited

U.S. PATENT DOCUMENTS

| | | | |
|---|---|---|---|
| 4,474,422 A | 10/1984 | Kitamura | |
| 4,796,997 A | 1/1989 | Svetkoff et al. | |
| 4,928,313 A | 5/1990 | Leonard et al. | |
| 4,933,754 A * | 6/1990 | Reed et al. ............ | 358/506 |
| 5,024,529 A | 6/1991 | Svetkoff et al. | |
| 5,351,067 A | 9/1994 | Lumelsky et al. | |
| 5,371,375 A | 12/1994 | Stern et al. | |
| 5,463,227 A | 10/1995 | Stern et al. | |
| 5,465,152 A | 11/1995 | Bilodeau et al. | |
| 5,475,370 A | 12/1995 | Stern | |
| 5,528,287 A | 6/1996 | Stern | |
| 5,532,738 A | 7/1996 | Stern | |
| 5,554,858 A | 9/1996 | Costa et al. | |
| 5,576,948 A | 11/1996 | Stern et al. | |
| 5,589,822 A | 12/1996 | Stern | |
| 5,600,150 A | 2/1997 | Stern et al. | |
| 5,617,076 A | 4/1997 | Stern | |
| 5,648,853 A | 7/1997 | Stern et al. | |
| 5,666,226 A * | 9/1997 | Ezra et al. ............ | 359/621 |
| 5,668,630 A | 9/1997 | Bilodeau et al. | |
| 5,691,544 A | 11/1997 | Stern et al. | |
| 5,691,810 A | 11/1997 | Bilodeau et al. | |
| 5,723,869 A | 3/1998 | Costa et al. | |
| 5,790,242 A | 8/1998 | Stern et al. | |
| 5,793,051 A | 8/1998 | Stern et al. | |
| 5,796,508 A * | 8/1998 | Suzuki ............ | 359/224.1 |
| 5,808,797 A | 9/1998 | Bloom et al. | |
| 5,818,061 A | 10/1998 | Stern et al. | |
| 5,838,239 A | 11/1998 | Stern et al. | |
| 5,841,538 A | 11/1998 | Schoeffler et al. | |
| 5,850,284 A | 12/1998 | Schoeffler et al. | |
| 5,859,924 A | 1/1999 | Liu et al. | |
| 6,031,225 A | 2/2000 | Stern et al. | |
| 6,036,096 A | 3/2000 | Evers et al. | |
| 6,060,224 A * | 5/2000 | Sweatt et al. ............ | 430/395 |

(Continued)

Primary Examiner — Sang Nguyen
(74) Attorney, Agent, or Firm — Dicke, Billig & Czaja, PLLC

(57) ABSTRACT

A manufacturing method and system are disclosed for illuminating a target. A light controller has a plurality of pixels, and light is projected from at least a first light source to the light controller, wherein the light from the first light source is incident on the light controller at a first angle. The pixels are controlled to establish illumination characteristics for first and second optical paths between the light controller and the target.

22 Claims, 11 Drawing Sheets

U.S. PATENT DOCUMENTS

| | | |
|---|---|---|
| 6,066,857 A | 5/2000 | Fantone et al. |
| 6,075,883 A | 6/2000 | Stern et al. |
| 6,098,887 A | 8/2000 | Figarella et al. |
| 6,181,472 B1 | 1/2001 | Liu |
| 6,244,764 B1 | 6/2001 | Lei et al. |
| 6,267,294 B1 | 7/2001 | Stern et al. |
| 6,283,374 B1 | 9/2001 | Fantone et al. |
| 6,291,816 B1 | 9/2001 | Liu |
| 6,293,408 B1 | 9/2001 | Behnke et al. |
| 6,311,886 B1 | 11/2001 | Alexander et al. |
| 6,325,272 B1 | 12/2001 | May et al. |
| 6,330,521 B1 | 12/2001 | Hahn et al. |
| 6,349,023 B1 | 2/2002 | Greenberg |
| 6,407,810 B1 | 6/2002 | Liu et al. |
| 6,429,934 B1 | 8/2002 | Dunn et al. |
| 6,481,187 B1 | 11/2002 | Behnke et al. |
| 6,496,270 B1 | 12/2002 | Kelley et al. |
| 6,500,378 B1 * | 12/2002 | Smith ............................ 264/401 |
| 6,525,827 B2 | 2/2003 | Liu |
| 6,566,627 B2 * | 5/2003 | Brandinger et al. ..... 219/121.69 |
| 6,573,987 B2 | 6/2003 | Shires |
| 6,585,185 B1 | 7/2003 | Weiss et al. |
| 6,603,874 B1 | 8/2003 | Stern et al. |
| 6,661,521 B1 | 12/2003 | Stern |
| 6,667,762 B1 | 12/2003 | Bouvier et al. |
| 6,750,899 B1 * | 6/2004 | Fishbaine et al. .............. 348/126 |
| 6,781,691 B2 * | 8/2004 | MacKinnon et al. .......... 356/326 |
| 6,788,416 B2 * | 9/2004 | Reuter ........................... 356/445 |
| 6,860,428 B1 | 3/2005 | Dowling et al. |
| 6,944,324 B2 | 9/2005 | Tran et al. |
| RE38,880 E | 11/2005 | Behnke et al. |
| 7,154,660 B2 * | 12/2006 | Reuter ........................... 359/291 |
| 7,158,238 B2 * | 1/2007 | Latypov et al. ................ 356/520 |
| 7,180,084 B2 | 2/2007 | Weiss et al. |
| 7,181,112 B2 * | 2/2007 | Harris ............................ 385/100 |
| 7,453,580 B2 | 11/2008 | Koh et al. |
| 7,459,333 B2 * | 12/2008 | Richards et al. ................. 438/66 |
| 7,492,378 B2 * | 2/2009 | Nishino et al. ................. 345/694 |
| 7,532,323 B2 * | 5/2009 | Tang et al. ..................... 356/317 |
| 7,580,559 B2 | 8/2009 | Latypov et al. ................ 382/152 |
| 7,652,765 B1 * | 1/2010 | Geshwind et al. ............. 356/330 |
| 7,692,784 B2 * | 4/2010 | MacKinnon et al. .......... 356/300 |
| 7,755,832 B2 * | 7/2010 | MacAulay ..................... 359/388 |
| 7,817,330 B2 * | 10/2010 | Arai et al. ...................... 359/290 |
| 2006/0158664 A1 | 7/2006 | Koh et al. |
| 2007/0019856 A1 | 1/2007 | Furman et al. |
| 2007/0285345 A1 * | 12/2007 | Nishino et al. ..................... 345/6 |
| 2009/0051929 A1 | 2/2009 | Koh et al. |

* cited by examiner

INSPECTION SYSTEM AND METHOD

CROSS-REFERENCE TO RELATED APPLICATION

This application is a continuation of International Patent Application No. PCT/US08/59031 designating US, filed on Apr. 1, 2008, which claims priority to U.S. Provisional Patent Application Ser. No. 60/909,862, filed on Apr. 3, 2007, both of which are incorporated by reference.

BACKGROUND

Many manufacturing processes electronic for electronic components and assemblies include inspection and test procedures, which can be either manual or automated. For example, the surface mount assembly process (SMT) consists fundamentally of three value added process steps: Solder paste printing, component mounting and reflow. These are schematically illustrated in FIG. 1. Un-stack bare board 30 removes a single bare circuit board from a stack of them and inserts it into the assembly line. Solder paste print 32 prints solder paste onto the bare circuit board. Component mount 34 moves components from a component bulk feed apparatus (not shown) and places them onto the circuit board. Reflow oven 36 melts the solder paste and then allows it to cool and re-solidify. Stack populated board 38 takes at least partially assembled circuit boards and stacks them into an easily portable batch.

There are many extensions and variations to the above, including inspection and test strategies, flipping the circuit boards so that components can be mounted onto each side, accommodation for through-hole components, glue deposition for those components that need to be held during assembly, odd-form assembly, under fill of flip-chip components, etc. But at its most basic level, the above steps describe the SMT line.

While the SMT assembly process has been refined, SMT assembly lines continue to make a variety of errors that lead to defective assemblies. These errors are herein grouped into classes:

One class of errors is related to solder paste printing and includes (non-exhaustive list): Incorrect height, volume or area of each individual solder paste deposit; Incorrect position (sometimes called solder paste registration errors); and Creation of a solder bridge (paste connecting two nominally separate deposits).

Another class of errors is related to components and includes (non-exhaustive list): Missing components (one or more not located where they should be); Extra components (one or more located where they shouldn't be); Incorrect components (wrong component type or value); and Incorrectly positioned components (linear or rotational errors).

Yet another class of errors comes from the reflow oven (non-exhaustive list): Incorrect temperatures; Incorrect dwell time in temperature zones; and Uneven heating.

Yet another class of error comes from raw materials imperfections (non-exhaustive list): Component lead oxidation; Component lead non-coplanarity; Panel (circuit board) surface contamination; Panel warp; Panel stretch (relative to the solder paste stencil); Stencil stretch (relative to the panel); Stencil apertures incorrectly sized, shaped, positioned; and Insufficient solvents in the paste.

Yet another class of error comes from design imperfections (non-exhaustive list): Components are placed too closely together or otherwise positioned so that, when the panel is in the oven, uneven heating causes solder paste to melt in a non-uniform way; and Copper pads and/or solder mask are incorrectly sized/positioned causing incorrect solder wicking.

Most of these errors have some visible manifestation when viewed after solder reflow. These manifestations include (non-exhaustive list): Missing components (compared to the design intent); Extra components (compared to the design intent); Wrong component (as compared to the design intent); Wrong value (e.g., the resistance or capacitance of a component is not correct, even though the package is right. This is a subset of wrong component); Tombstone (a two lead component flipped up on end so that it is making contact only on one lead); Billboard (a two lead component flipped up on its side so that it is making contact on both leads, but not with a correct solder fillet); Dead Bug (a component flipped upside down "feet up"); Wrong polarity (a device whose orientation must be controlled for correct electrical behavior but is oriented incorrectly); Bad solder joint (one or more solder joints is improperly formed. Solder joints that are located under the body of a component would not normally be visible but can be observed via x-ray inspection); Lifted lead (not all the leads of a component are soldered well to the panel. Caused by component coplanarity errors, panel warp or both); and Solder bridge (two leads that should be electrically isolated have electrical continuity).

Defects can result in electronic assemblies that do not work correctly while they are still in the factory. It is possible to catch most of these before the assembly is shipped by electrically testing the completed assembly, depending on the thoroughness of the test. Thorough electrical testing is often quite difficult and time consuming, especially for more complex electrical assemblies. For some devices, thorough electrical test is so difficult as to be considered impractical.

Sometimes, assemblies will work properly when electrically tested at the factory and then fail after only a short time in the field. These failures are often caused by visually evident errors. For example, a partially formed solder joint will provide good electrical contact but possibly tenuous mechanical contact. Thermally or mechanically induced physical stresses can cause this solder joint to crack leading to premature field failure. However, improperly formed solder joints can be visually detected if they are not hidden from view (e.g. by a component body or a radio frequency (RF) shield, or the like).

Accordingly, electrical test is generally understood to be an incomplete quality control approach. To supplement electrical test, SMT operators nearly always implement some sort of visual inspection approach at the end of the assembly line (after reflow). One type of inspection is by human visual. Another, often more suitable approach, is in-line AOI (Automatic Optical Inspection) and sometimes X-Ray (automatic or manual) inspection.

AOI machines are nearly always two dimensional (2D); that is they acquire (most often) color images of the assembled panel and analyze the luminance and chrominance characteristics of those images to determine if the appearance of the panel is acceptable according to criteria established through the programming efforts described above.

Three dimensional (3D) AOI machines, while uncommon, are known. 3D AOI machines offer the advantage of detection of the relevant attributes of a component such as its presence and position at least in part based upon its height, rather than solely upon its luminance or color. The key advantage of this method is that all components, because of their basic mechanical nature, will stand up above a substantially planar substrate or panel. As stated above, 2D AOI machines must be sensitive to the component's appearance, which can change from vendor to vendor and, at the extreme, could be the same as the panel thereby making it invisible to a 2D sensing methodology.

3D AOI has not generally been adopted in the SMT industry because it is complicated, slow (the scan time is long) and expensive compared to 2D AOI. Also, a height map of a component on a panel is insufficient to determine all the interesting characteristics of a panel, so a system that only acquired 3D data would be insufficient to screen for all of the possible errors detectable after SMT reflow.

There are many extant methods for acquiring height data on the scale required for 3D AOI. Among them are: Laser triangulation; Shadow casting; and Phase Profilometry.

The best method will depend upon the target's optical and mechanical characteristics, the requirements for speed and cost and the nature of which exact measurements are needed.

Laser triangulation is widely used and can be accomplished by projecting a spot or a line or a series of lines onto the target. Spot projection, see FIG. 2, has the advantage of wide dynamic range, but is very slow compared to line projection techniques. In FIG. 2, which is a simplified schematic side view, a spot projector 21 generates directed light 22 to illuminate a target 18 situated on a substrate 10 with an optional substrate top coating 11. In the illustrated configuration, light from the spot 23 striking the top of the component 18 is diffusely scattered and some of this scattered light is collected by light receiver 24. Light scattered from spot 23 appears to camera 24 to shift laterally depending on the height 19 of the scattering surface 18. Note the coordinate system 20 wherein "height" is meant to be substantially parallel to the Z direction.

Referring to FIG. 3, which is a top view and is schematically what the light receiver 24 of FIG. 2 sees as it looks down on the scene. Referring to coordinate system 20, spot 5 has a certain position in the X direction in the image. If the object with height 18 were missing from the scene, the directed light 22 would strike the substrate top coating 11 and the spot would appear to scatter light from position 6. The apparent lateral X displacement between position 5 and position 6 is thus an indication of the height of the top surface of object 18 above substrate top coating 11.

While they can be very accurate, simple spot range measurement techniques are slow, because the height is measured from only one spot a time. A spot scanning mechanism such as a moving mirror, an Acousto-Optic Deflector (AO cell) or the like is often used to speed this up but these approaches add substantial complexity and cost. High speed spot projectors are implemented with high power lasers in order to generate the required signal within a short time. These require safety precautions according to rules established by the US FDA.

Line scanners can be faster than spot projectors but suffer from multi-path (reflections from nearby targets) and do not have as wide a dynamic range. However, they are typically cheaper and simpler than spot based laser triangulation systems with scanners and may possibly be operated at lower power levels than spot projectors.

FIG. 4 illustrates how the scanning spot and line projector systems work. The light projector 21 directs a flying spot or a sheet of light 22 onto feature with height 18 above substrate 10. The camera, omitted from this drawing for clarity, will observe light scattered from illuminated line segments 5 and 6. Line segment 5 is returned to the camera from the top of the feature with height 18. Line segments 6 are returned from the substrate 10. The lateral X displacement of points along line segment 5 from points along line segments 6 is a measure of the heights of those points relative to one another. Distinct from the spot scanner of FIGS. 2 and 3, in this case, a plurality of height measurements is available because data from multiple points on each line have been acquired.

For a given cost or complexity, phase profilometry is the fastest known method because a potentially large 2D area of the target can be illuminated at once (as compared to a spot or a line). Phase profilometry is also most often implemented with white light from a strobe or other light source and is therefore not subject to FDA laser safety considerations.

The technique of phase profilometry is widely used for forming height maps of substantially diffuse targets. See for example U.S. Pat. No. 4,641,972 (incorporated by reference). This technique is also used for forming height maps of highly specular targets such as mirrors. For the former use, the illuminator is at a non-specular angle from the image acquisition optics (as was the case for the spot range finder of FIG. 2). For the later use, the illuminator and the acquisition optics are arranged to be substantially at the specular angle (not illustrated).

A significant component in a phase profilometry system is a structured light projector, shown schematically at 21, 30, 31 and 32 in FIG. 5, which replaces the spot or line projectors of above. This projector differs from the line projector in that, instead of projecting light along a thin sheet that when striking the target surface makes a contour, this projector projects intensity modulated light 22 along a volume that when striking the target surface, illuminates a two dimensional area on that surface with that intensity pattern.

In FIG. 5, light 22 striking the target surface of object 18 is scattered diffusely as before and again, some of it is captured by camera 24. The scattered light that enters the camera is illustrated in this drawing as ray 36 but it should be construed to a volume of light that will form a 2D image within camera 24.

Like the line and spot projectors of FIGS. 2 through 4, the light is projected along a first direction. Camera 24 observes the scene from a second or observation direction. These two directions are not parallel and the included angle 34 between them is called the triangulation angle. In FIG. 5, the observation direction is substantially perpendicular to the substrate surface 10. A pattern is superimposed up the projected light such that the pattern, or portions thereof, will appear, when viewed by the camera 24, to shift laterally as it strikes objects of varying height. This lateral shift, which in a repetitive pattern can be considered a phase shift, is indicative of the heights of an area of points on the surface in the same general way as the lateral shift of the spot or the line is so indicative of a single point or a linear grouping of points.

The advantage of the line projector over the spot projector is that height data of a plurality of points along the illuminated contour can be acquired instead of only at the one illuminated spot.

Phase profilometry has an advantage over the line projection technique in that height data of a plurality of points in the illuminated area can be acquired instead of only along the one illuminated line.

Referring still to FIG. 5, light from light projector 21 passes through reticle or grating 30 and is directed onto target 18 and top surface of substrate 10 with optional coating 11. Light scattered from target 18 is captured by receive optical system 33 and passed to camera 24 for later processing by electronics (not shown).

Although FIG. 5 is a 2D drawing, it will be understood that the light 22 from projection system 21, 30, 31, and 32 is illuminating an area of the top surface of target 18 and top surface of substrate 10 or coating 11.

There are numerous ways to introduce the pattern to the projected light (non-exhaustive list):

1. Projection of light through a square wave grating or ruling generating square wave patterns on the target.
2. Projection of light through a pixilated grating allowing for generation of sinusoidal patterns. Usually some sort of spatial low pass filter is employed to suppress the pixelization leaving only the low frequency sinusoid.
3. Defocusing of the above to suppress harmonics (in the case of -1-) or the individual pixels (in the case of -2-)
4. Astigmatic projection of a sinusoidal pattern to generate a sinusoidal pattern.

The classic characteristics of the projector for SMT inspection are:

Sinusoid projection pattern.

Telecentric optics providing substantially constant magnification over changing distance from the projector to the target surface.

Scheimpflug condition optics for the projector: Referring to again FIG. 5, the projected patterned light beam 22 is at an angle 34 from the normal to the top substrate surface 10 and 11. A projection system that conforms to the Scheimpflug condition allows the projected pattern's focal plane to be parallel to the target surface even when the optical axis is off normal. Satisfaction of the Scheimpflug condition requires the reticle or grating 30 to be rotated from the optical axis of the projector.

Classically, three images are acquired of substantially the same field of view. The three images are such that the phase of the projected pattern is changed for each of them; usually the phases are 0, 120 and 240 degrees. Other combinations of phases can work and are sometimes used for mechanical convenience. Three images are the minimum required to unambiguously resolve the three inherent ambiguities of the target which are:
1. Brightness
2. Vector Phase
3. Vector Length The Brightness refers to how bright a region of the target is as measured by the amount of structured light observed returning from that region to the observation camera.

The Vector Phase refers to the observed phase of the projected pattern as modified (shifted laterally) by height features on the target. When an idealized projector projects the pattern onto a flat planar surface devoid of height features, the Vector Phase will change according to the projection frequency only. In the presence of height variations, the phase will vary from the above in relation to those height variations.

The Vector Length refers to the fraction of the projected modulation that is returned from a region on the target to the camera. It can be used to determine the reliability or quality of the measurement of the Vector Phase; the smaller the Vector Length, the noisier the Vector Phase.

All three of these unknowns can be unambiguously solved by the application of public domain phase reconstruction algorithms to the three images taken at 120° phase shift from each other, or to four images taken at 90° phase shift from each other, or to any n images, $n \geq 3$, where the phase shift between the images is known, not zero, and not 360° or a multiple thereof.

Exemplary reconstruction equations and an approach for the three image reconstruction are disclosed in U.S. Pat. No. 6,750,899 B1, which is incorporated by reference. According to the '899 patent, a generalized approach allows us to compute H from images where the phase differences between successive images are known but unequal. The normalized intensity value for each pixel in the three-image co-sited set is given in Equation 1):

$$\begin{pmatrix} A \\ B \\ C \end{pmatrix} = r \begin{pmatrix} 1 + m\cos(\phi - \phi_a) \\ 1 + m\cos(\phi - \phi_b) \\ 1 + m\cos(\phi - \phi_c) \end{pmatrix}$$

where r is the normalized reflectance at the pixel (the brightness), the known phase angles of the three fringes are $\phi_a$, $\phi_b$, $\phi_c$ and the relative phase $\phi$ of the fringe at the pixel is related to the projected fringe frequencies, pixel coordinate and z position by Equation 2):

$$\phi = 2\pi(f_x x + f_y y + f_z z)$$

To linearize the problem and make it more easily computed, the quantities are defined as in Equation 3):

$$x = m \cos \phi$$

$$y = m \sin \phi$$

Then, Equation 1) can be re-written as in Equation 4):

$$\begin{pmatrix} A \\ B \\ C \end{pmatrix} = \begin{pmatrix} 1 & \cos\phi_a & \sin\phi_a \\ 1 & \cos\phi_b & \sin\phi_b \\ 1 & \cos\phi_c & \sin\phi_c \end{pmatrix} \begin{pmatrix} r \\ x \\ y \end{pmatrix}$$

Through standard linear algebra, the system matrix in Equation 4) can be solved for r, x, and y. From x, y, the phase $\phi$ of the pixel can be computed by the processor in Equation 5):

$$\phi = \tan^{-1}(y/x)$$

Once the phase $\phi$ is computed in Equation 5), we multiply by an appropriate calibration scaling factor to compute the height of the pixel. Once all the heights for all the pixels are computed, the height map, H, is completed and ready for summary processing and display, as appropriate. An example height map is shown in FIG. 4A of the '899 patent.

Note that the above approach is only one of numerous formulations for arriving at the phase, and therefore the height map, from $n \geq 3$ phase shifted images.

As mentioned, the classic projection optical arrangement is telecentric. However, telecentricity is expensive and bulky to implement. Digitally correcting for non-telecentricity is known, but it is computationally intensive. Telecentricity has been chosen despite its drawbacks because it eliminates the compute burden required to correct the image for effects caused by variable range to the target. In the interests of the high throughput speeds required of in-line systems, this has been an appropriate tradeoff.

Off-line inspection systems, however, do not have the same high throughput speed requirements, so the extra cost and bulk of a telecentric projector is wasteful for that use.

There are numerous ways to generate images with the required phase shifts. One is to move an entire camera/projector assembly relative to the target. The phase pattern projected onto the target will shift accordingly. Re-registering the acquired image based on knowledge of the physical distance traversed will yield the required images. This method sacrifices a portion of the field of view but offers the advantage of opto-mechanical simplicity. Also, when coupled with a strobe lamp based illumination system, this method can provide the advantage of high speed. The motion system however must be very precise so as to allow re-registration to occur with the required precision; about one to two microns when used for solder paste inspection. Also, there are stringent demands placed upon the maximum allowable distortion of the optics in such a system. The required motion precision and high quality optics can make such a system expensive. There is at least one extant mechanism that operates this way.

Another approach is to keep the camera substantially stationary relative to the target and move the projector or an optical element within it so as to cause the projected fringe pattern to shift the desired amount. Referring again to FIG. 5, mechanical actuator 31 causes reticle or grating 30 to move a small distance between image acquisitions by camera 24. This small distance causes the projected pattern 22 to shift accordingly thereby introducing the required phase shift between image acquisitions. There are many electro-mechanical ways to do this including the use of moving mirrors or refractors. This motion must also be precise, or at least, precisely known, in order to be sure that the phases of the projected pattern have the right, or at least precisely known, phase shifts between them. Errors in this motion result in incorrect computation of the Vector Phase and therefore the heights. Incorrect height measurements can lead to False Calls (occurrences where the inspection device detects an error when, in fact, none is present) or False Accepts (occurrences where the inspection device determines that no error is present, when in fact one is). These motion systems can be costly, bulky, may have physical wear concerns leading to breakdowns or periodic service requirements and may be slow.

All the above mentioned mechanisms are incapable of removing the pattern from the projected light.

Though some of them, as illustrated in FIG. 5, are able to internally shift the phase of the projected pattern, none are capable of changing the spatial frequency of that pattern because it is substantially fixed by the optics 32 and the nature of the pattern of the reticle or grating 30.

One significant challenge relating to the use of phase profilometry to form height images of a circuit board is the mix of specular and diffuse features on the target surface. An example of a diffuse feature is the top a textured, typically grey component. An example of a specular feature is a solder joint or the top of a shiny component.

Shiny features that happen to be oriented so as to reflect light from the illumination system directly into the camera will appear to be very bright and will saturate the imager (e.g. CCD or CMOS area array or the like) located in the camera. The precise quantification of received light required to perform accurate phase profilometry will be lost for those pixels that are saturated. In the worst case, these very bright features can cause blooming on the imager, a phenomenon that will corrupt nearby pixels. At the other extreme, shiny features that are oriented so as to reflect light entirely away from the illumination system will appear to be very dark, so that again, the precise quantification of light required for accurate height calculations will be inhibited by various sources of noise (e.g. shot noise, dark current, quantification, etc.).

For this reason, forming a high fidelity height map of this mix of features from a single sensor system requires that system to have a very large dynamic range, preferably on the order of five decades. A large dynamic range allows bright reflections from specular surfaces to be imaged without saturation or blooming while also allowing data from dark areas to be acquired with an acceptable signal to noise ratio (SNR). Laser point range sensors can achieve this dynamic range at the cost of extremely slow throughput.

Techniques to extend the dynamic range of area based imagers are known and used in digital photography. Typically, images—of a scene with varying and precisely known exposure times are acquired, for example one under exposed, one properly exposed and one overexposed. These images are then merged according to some rule related to the exposure times and apparent brightness of the three images on a pixel by pixel basis. For example, saturated pixels in the overexposed image are not used. Instead, values for those pixels are used from either the properly exposed image or the under exposed image and then scaled according to the precisely known exposure time. The dynamic range of the resulting composite image can be orders of magnitude greater than that of any one single image, depending on the ratio of the exposure times.

Of course, this approach is not easily adaptable to moving scenes. US Patent Publication No. 2002191834 teaches a way to achieve this function with moving scenes using a strobe lamp.

Systems with only three orders of dynamic range are known to work well enough for SPI, because solder paste before reflow behaves, in aggregate, substantially like an optically diffuse surface. However, when components are added and especially once solder paste is reflowed; the specular or shiny conditions described above occur in abundance throughout the assembled circuit board.

One of the problems with phase profilometry is the ambiguity caused by 360° phase shifts. Slowly (spatially) shifting phase, where the spatial sampling density is in excess of the Nyquist limit, can be accommodated by phase unwrapping algorithms, but sudden changes are inherent in many target surfaces present in the SMT application, especially for components on panels. Phase unwrapping would be very unreliable in this application.

If the sudden changes are limited in size to substantially less than 180°, then the phase is readily computable without resorting to phase unwrapping. Solder paste deposits tend to be approximately 200 µm in height or less, so an appropriate phase wrap height to choose for this application is 500 µm or so, and under these conditions, phase unwrapping is unneeded.

However, for 3D AOI, the target surface can have sudden height changes on the order of 20 mm. For this application, a phase wrap height would preferably be 50 mm or so.

Referring to FIG. 6, the pattern projector 40 (considered to include everything required to project a pattern onto the target surface, including the light source, pattern introduction means and optics) illuminates an area 41 on the substrate surface 10 with optional coating 11. The illumination area 41 projects partially onto object with height 18. The pattern is an intensity modulated sinusoid with wave crests or troughs illustrated schematically by parallel lines 46 and 47.

Lines 46 are illuminating the top surface of the substrate 10 and can be used to compute the height of points on that surface. Lines 47 are illuminating the top surface of the object with height 18. The lateral shift 48 between points on these lines is a measure of the height difference between points on the substrate surface and points on the object with height surface.

The wave pattern has a wave direction 42. In this example, the wave direction 42 is not parallel to the projection azimuth angle direction (angle 44 to the X axis 20) and the included angle between the two is shown at 45.

Referring to FIGS. 5 and 6, increasing the wrap height (the height step that corresponds to a 360° phase shift in the repetitive projection pattern) can be done by increasing the wavelength of the projected pattern or decreasing the included angle 34 of FIG. 5 between the source and the receiver, or increasing the included angle 45 of FIG. 6.

However it is done, increasing the wrap height has the negative effect of decreasing the system's sensitivity to Z height changes, essentially reducing the system's resolution in that direction.

The preferred condition for an inspection system suited to both 3D SPI and 3D AOI is to have the high Z sensitivity concomitant to a short wrap height and have the phase determinism concomitant to a large wrap height.

As of this writing, all known phase profilometry approaches use a fixed wavelength phase projector with a fixed included angle 34 of FIG. 5 and with a fixed included angle 45 of FIG. 6 and are therefore unable to vary their wrap heights.

The use of three phase projections, where classically a phase shift of 120° is used there between to generate patterns from which a height map can be made, does not measure r directly. If r can be measured directly, and if multiple patterns, for example of varying wavelength, are used to extend the wrap height, then one r can be used to normalize two or more sets of x and y, thereby reducing the number of images that must be acquired.

Extant phase profilometry systems have fixed illumination azimuth angles 44 of FIG. 6. Most often, only one such angle is used. One system is able to use two fixed illumination azimuth angles wherein a single projector is used to illuminate a macroscopically moving mirror that directs the projected pattern to one or another of two physically distinct optical systems, comprised of mirrors, and deployed to project light either at illumination azimuth angle 44 of FIG. 6 or that angle+180°. The advantage that two illumination azimuth angles yields relates to shadows. Height objects with sharply rising sides may have a portion of their surface in shadow when only one illumination azimuth angle is used. In that case, information from the shadow region is unavailable to the inspection system. Thus a projection system able to use two illumination azimuth angles offset from one another by 180° has an increased probability of being able to acquire data from the shadow region at the expense of increased data acquisition time (time for the moving mirror to move and settle plus time the additional images to be acquired), data processing time and increased mechanical complexity (the moving mirror).

In the above mentioned system all the projection optics save the moving mirror are stationary. Thus the illumination azimuth angles are not variable but are fixed by the stationary optics and are selected for use, one at a time, by the macroscopically moving mirror.

The above approach works well for solder paste inspection where all the height features (solder paste) are at nearly the same height. Solder paste deposits, when printed properly, are spaced so that two illumination azimuth angles offset by 180° from each other will almost certainly allow for a view of the entire surface of each deposit.

However, for 3D AOI, where targets of interest with substantially different height may be situated adjacent to each other, no specific predetermined, fixed illumination azimuth angle or even pair of such angles can be assured of casting light onto the shorter target. This is especially true for solder joint inspection. Solder joints have heights at elevations at or very near to the top surface of the circuit board; i.e. they are very short targets.

In-line solder paste inspection (SPI) is often used to screen out incorrect solder paste prints before an erroneously printed panel can proceed down the assembly line. These inspection machines are available to inspect solder paste in 2D or 3D. Solder paste printers often are able to implement in-printer inspection (both 2D and 3D are available) but the time available for in-printer inspection is severely limited by the throughput requirements of the line. 3D is preferred because a significant portion of the solder paste printing errors are detectable only by devices that are sensitive to height and volume, not just area and XY position. However, 3D inspection machines tend to be substantially more expensive and somewhat slower than 2D.

In-line 3D SPI machines are quite expensive (~US$100,000) and are sometimes difficult to program. They take up floor space in factories where this is sometimes at a premium. They cannot be used to service more than one line at a time.

In-line 2D SPI machines are less expensive (~US$60,000) and are often more difficult to program than 3D.

One of the costly subsystems in both for SPI and AOI machines is the transport mechanism. This allows the projector/camera subsystem to tour large regions of the circuit board, regions that are larger than the camera's field of view. For in-line systems, these mechanisms must move quickly, as time is of the essence. Also, for many extant systems, they must move precisely, because imprecision in their movement causes imprecision in their measurements related to X and Y target positions (a lateral error, one in the XY plane, of the target as compared to the design intent). Examples of these measurements are the solder paste registration and a component position error.

Some in-line machines are claimed to implement both AOI and SPI thereby permitting their owners to move those machines to either inspection point as required. The extant dual-mode machines are able to implement 2D AOI inspection only. Of course, when it is in-line, the machine can implement only one of these functions at a time.

If operated in an off-line way such extant dual-mode machines can be switched from one mode to the other. But they require the user to manually change sensor heads; one head is able to perform SPI, the other AOI, and only one head can be situated within the machine at one time. So switching from one mode to the other requires a time consuming physical reconfiguration of the machine. Additionally, it may be necessary to run different mode-specific software applications.

A single off-line dual-purpose machine able to perform both 3D SPI and 3D AOI would be able to merge data acquired during SPI functions with data acquired during AOI functions applied to the same panel. There are many ways data can be profitably shared. One such way relates to programming or training the system to perform SPI and/or AOI. Once the system is programmed to perform, for example, SPI, much of what is needed to train the system to perform AOI is already known. Other ways of sharing data related to training are disclosed in the incorporated PCT and U.S. Provisional Application.

Another way data can be profitable shared can be seen by considering that a particular instance of a panel is inspected for SPI and later, when components have been mounted and solder reflowed, again the same panel is inspected for AOI. If a defect was found at AOI inspection, whether or not a corresponding defect was found at the same location during SPI inspection, it would be advantageous to present to the user all data and images from the SPI observation of the relevant location. These data and images, 2D or 3D, can be useful in determining the cause of the failure detected at AOI.

Although software and specialized systems exist for this purpose, in-line inspection machines are unable to perform this merging of data by themselves, because they are different machines located at different points in the SMT line. However, two separate machines of the same design, one at the SPI location and the other at the AOI location, can share image data in the same way as a single dual-purpose machine, situated off-line. Profitable sharing of image data is facilitated because the optics of both machines are nominally identical, so "difference" based image processing is greatly facilitated.

Also, a single off-line machine able to perform both 3D SPI and 3D AOI would cost less than two special purpose machines, occupy less work space on often crowded shop floors, would naturally have a single user interface for users to learn, would require fewer spare parts and in general, be simpler and cheaper to use and maintain.

For these and other reasons, there is a need for the present invention.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

DETAILED DESCRIPTION

Figure 1:
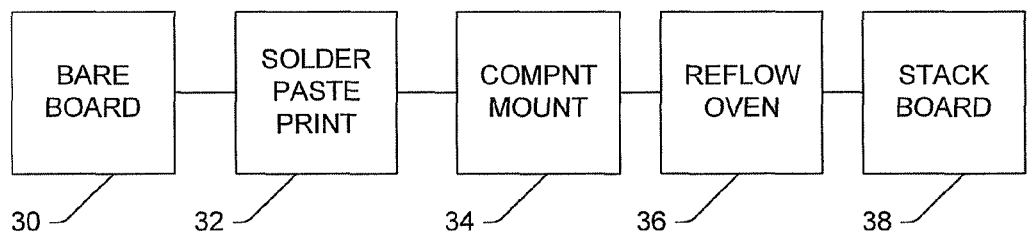
FIG. 1 schematically illustrates portions of an SMT assembly process.
Figure 2:
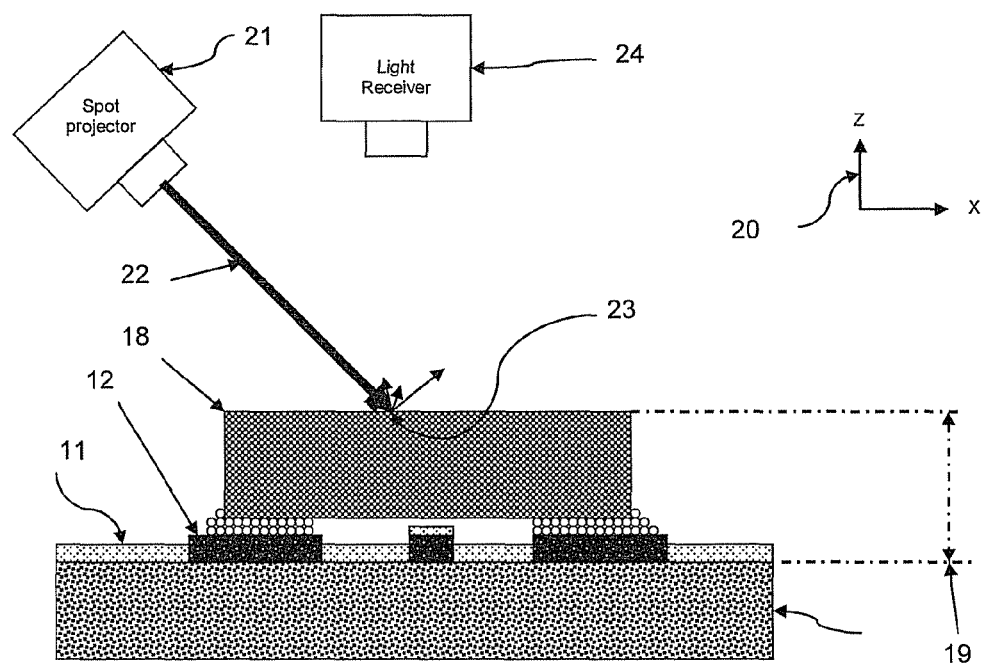
FIG. 2 is a simplified schematic side view illustrating a partially assembled circuit board and a point range measurement system.
Figure 3:
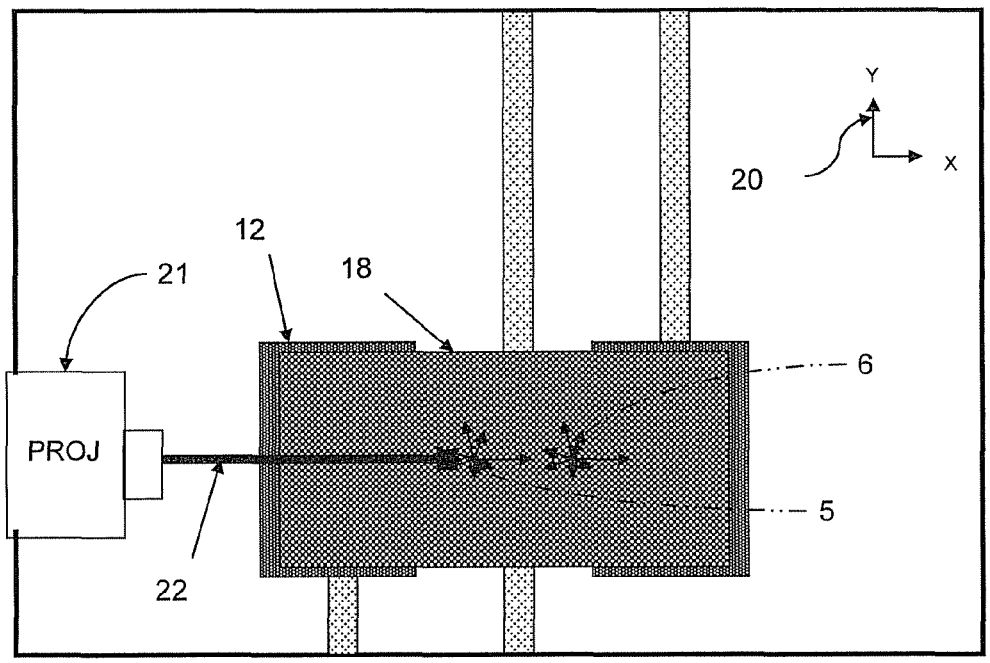
FIG. 3 is a simplified schematic top view illustrating a partially assembled circuit board and conceptually illustrating what the light receiver shown in FIG. 2 sees as it looks down on the scene.
Figure 4:
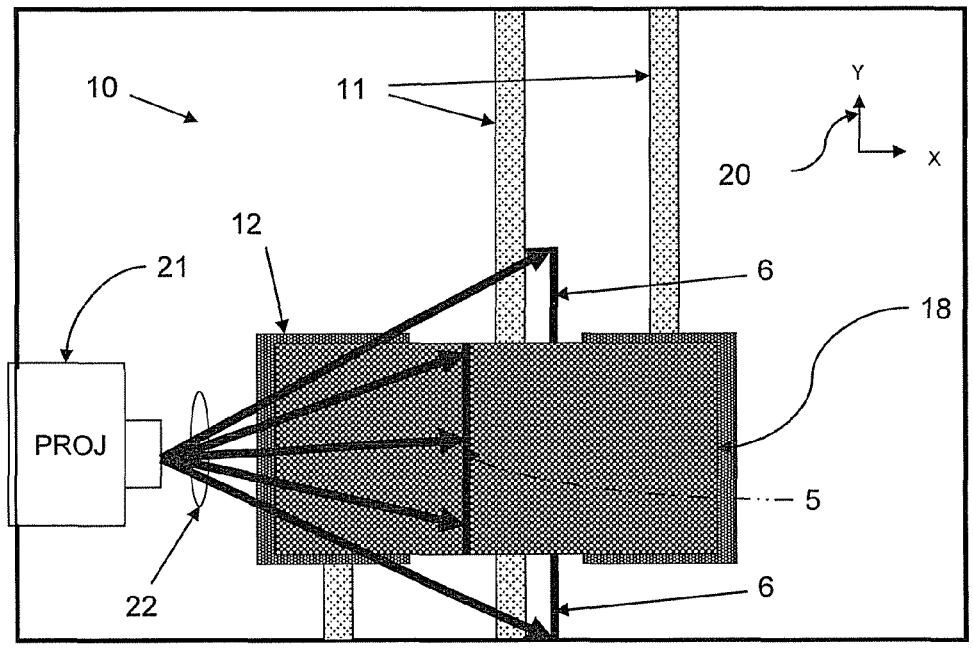
FIG. 4 is a simplified schematic top view illustrating a partially assembled circuit board and conceptually showing scanning spot or line projector systems operation.

In the following Detailed Description, reference is made to the accompanying drawings, which form a part hereof, and in which is shown by way of illustrating specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

In accordance with exemplary aspects of the present invention, an inspection machine is disclosed, where three dimensional (3D) phase profilometry and a two dimensional (2D) color camera are used to characterize the Device Under Test, typically but not limited to a circuit board, substrate or panel before and/or after various assembly steps or value add operations are performed on it. Among other things, the inspection machine is able to:

1. Vary the wrap height as is optimal for forming height maps given the conditions of the circuit board, substrate or panel;
2. Allow for the acquisition of multiple images, with varying illumination intensity and/or exposure times, in order to extend the dynamic range and to therefore allow for the generation of high fidelity height maps under a broad range of optical conditions;
3. Merge data and images acquired from multiple stages of circuit board assembly into one easily viewable data set to facilitate human understanding of the cause of detected failures;
4. Perform inspection at least in part based upon difference image processing using multiple images of a single instance of the circuit board, substrate or panel acquired before and after one or more value add operations;
5. Perform inspection at least in part based upon difference image processing when images of a single circuit board, substrate or panel have been acquired at more than one stage of assembly;
6. Perform inspection at least in part based upon difference image processing when images of multiple instances of a circuit board, substrate or panel of a given design, and therefore having the same nominal appearance, have been acquired at more than one stage of assembly;
7. Project upon the surface of the circuit board, substrate or panel, from a single set of projection optics, two or more fringe patterns of different phase, where the phase between them is precisely known and where no macroscopically moving parts are used to cause the phase shift;
8. Allow the pattern projector to deliver directional but unpatterned light to the surface of the circuit board, substrate or panel through the same optical system that delivers the patterned light;
9. Allow the pattern projector to modify the frequency of the projected pattern delivered to the surface of the circuit board, substrate or panel;

10. Allow the pattern projector to modify the wave direction of the projected pattern delivered to the circuit board, substrate or panel independently of the illumination azimuth angle;
11. Allow the pattern projector to continuously vary the illumination azimuth angle to a value best suited for the target condition;
12. Allow the pattern projector to select one of at least two optical subsystems, arranged so as to project at different azimuth angles from each other, quickly (compared to moving mirror systems) and without macroscopically moving parts;
13. Determine automatically, without human intervention, the value of the illumination azimuth angle best suited for the condition of the circuit board, substrate or panel;
14. Provide precise XY measurements of solder paste without requiring precise stage mechanisms;
15. Provide precise XY measurements of component positions without requiring precise stage mechanisms;
16. Determine metrics related to the quality of the assembly step or the value add operation based upon the acquired images;
17. Compare the metrics related to the value add operation to one or more thresholds, derived from CAD or example assemblies, Golden or not, or a mix, in order to determine the acceptability of the value add operation or assembly step;
18. Compare the metrics related to the value add operation to one or more thresholds, derived from CAD or example assemblies, Golden or not, or a mix, in order to automatically determine the category of error, if one has occurred;
19. Use the measurements of scanned circuit boards to establish a data base suitable for statistical process control (SPC) charts, warning and error thresholds;
20. Link images of scanned circuit boards to a data base so that users can view these images whether or not a failure has been detected;
21. Use images acquired from the 2D camera and/or 3D subsystem to determine the presence and XY location of marks on the circuit board, such marks being designed onto the bare circuit board for the primary purpose of being found and so located;
22. Use images acquired from the 2D camera and/or 3D subsystem to determine the XY location of features on the circuit board, such features being designed onto the bare circuit board for the primary purpose of conveying electrical signals from one or more points on the bare circuit board to another one or more points;
23. The use of high resolution 2D color images to allow the user to view, with high magnification, the circuit board.

Figure 5:
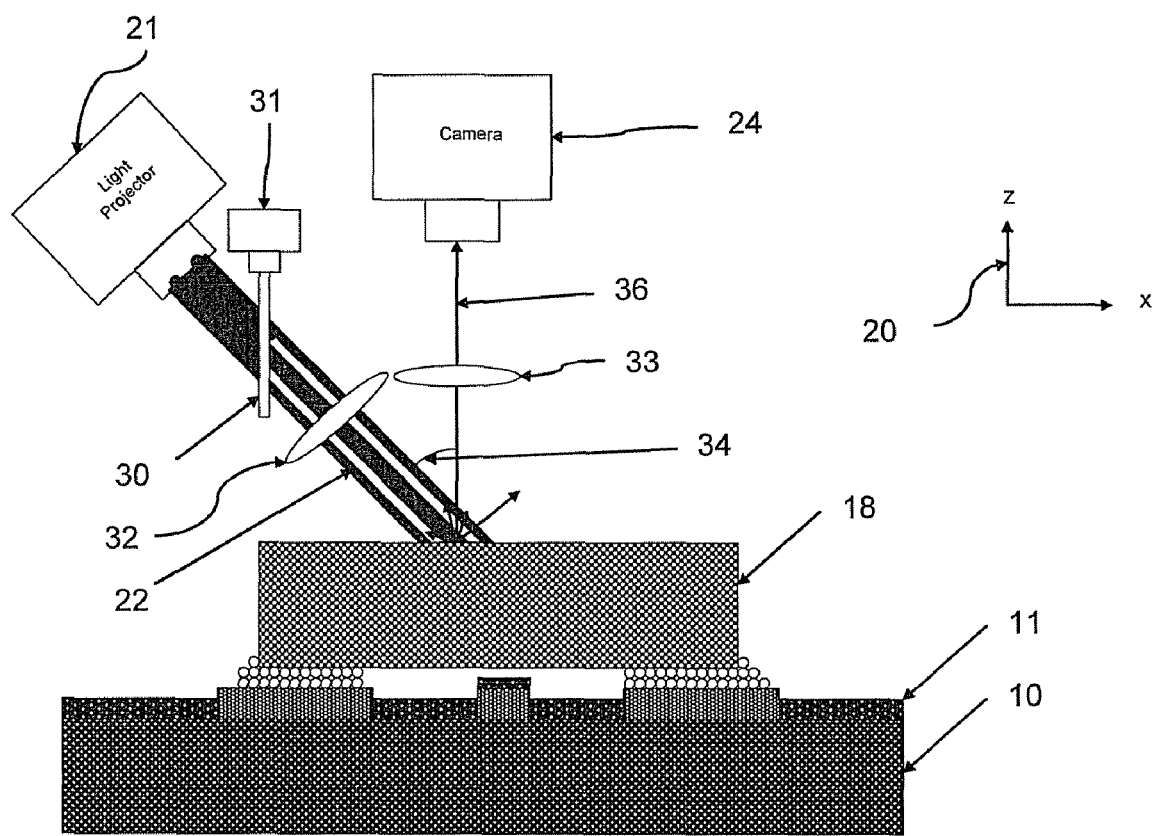
FIG. 5 is a simplified schematic top view illustrating a partially assembled circuit board and conceptually showing a phase profilometry system operation.
Figure 6:
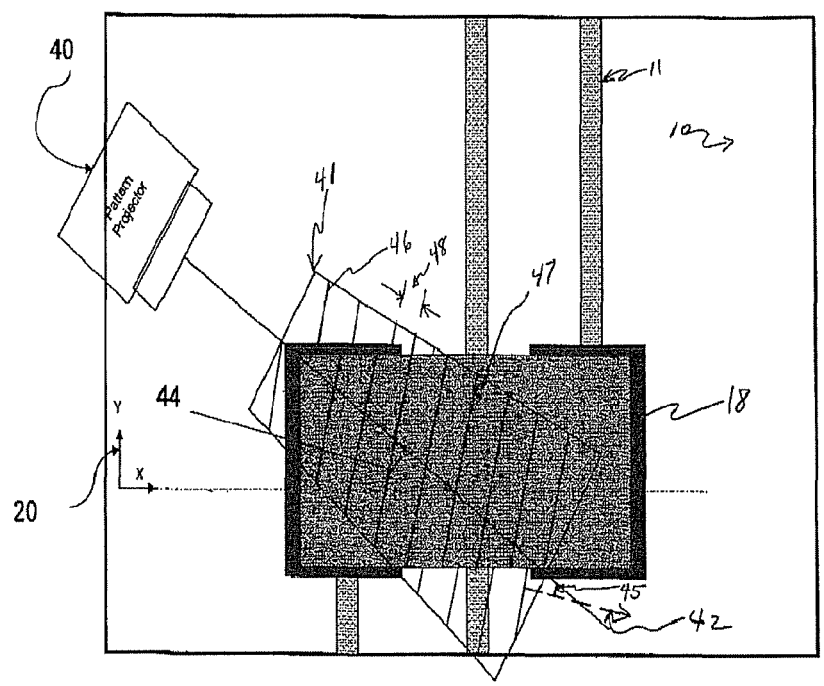
FIG. 6 is a simplified schematic top view illustrating a partially assembled circuit board and conceptually showing a pattern projector operation.

Referring again to FIG. 5, the grating or reticle 30 introduces the intensity modulation to the projected light. Actuator 31 is moves the grating or reticle 30 to introduce the required phase shift(s).

Replacement of reticle or grating 30 with a light controller including, for example, a transmissive LCD and actuator 31 with suitable LCD control electronics allows controlling light from a light source at a pixel level to illuminate a target with more than one illumination characteristic. This allows for varying patterns to be used, these patterns typically being under control of a computer (not shown). Thus, the computer has direct control over the illumination characteristics of the light delivered to the target, including but not limited to the phase, wavelength and wave direction of the pattern, and can therefore adjust the wrap height without resorting to mechanisms with moving parts. Other computer controllable image projection devices are available, for example micro-mirror arrays such as "DLP chips" or liquid crystal on silicon devices known as "LCoS chips". Approaches using these devices are included in the system of this invention; for the purpose of controlling the projected pattern, they can be used in lieu of the LCD with only minor changes. Although the micro-mirrors of a DLP chip move, this motion is not "macroscopic" in that: (a) each mirror corresponds to an individual pixel (rather than an entire image as is the case in the prior art discussed above); (b) each individual mirror is tiny (15 μm) and (c) each mirror moves very quickly (~10 μsec).

Additionally, the pattern can be removed entirely, thereby allowing directional light without modulation to strike the target. An image acquired under these conditions yields directly the local reflectivity map r required for height reconstruction as described in equations 1 through 5 above.

Therefore, if more than one set of images is used to generate height maps of differing wrap heights, the single reflectivity map r can be used to normalize both. This reduces the total number of images required.

Because the transparency of a given pixel within a light controller comprised of a transmissive LCD can be controlled digitally, the illumination characteristic of intensity of the delivered light can be adjusted without changing the intensity of the light source 21. This ability to control the intensity of the delivered light, in conjunction with varying the exposure time of the camera, can be used to extend the dynamic range. One way to do this is to take two or more exposures with a given pattern. As described above, pixels that are saturated in the long exposure/bright light condition are replaced with those taken in a shorter exposure and/or dimmer light condition and scaled according to the precisely known exposure time and brightness values. The exposure time can be very well known as it is controlled electronically within the camera using standard techniques. The brightness can also be precisely known but may require a calibration step wherein different values of LCD transparency are mapped to different observed brightness levels under controlled conditions, for example, using a constant brightness target. A good example of such a target is white paper. These two controls, the LCD transparency and the exposure time, are preferably adjusted so that the range of exposures covers two orders of magnitude, thereby extending the three orders of dynamic range available within the camera to the five orders required to generate high fidelity height maps in the presence of specular and diffuse conditions that exist on the populated circuit board, especially after reflow.

Other ways to extend the dynamic range using multiple exposures exist but they are similar to the above method because they all rely, in some way or another, on detecting, in one or more images (or values derived therefrom) the condition and the locale of under or over exposed pixels; pixels whose proper digital value is unknown or poorly known. Images acquired under differing exposure and illumination conditions are then used to generate pixels (or values derived therefrom) in the corresponding locales whose digital values are known or better known.

One example of another such method uses three phase shifted images acquired under a first set of identical exposure and illumination conditions; these conditions intended to avoid saturation at substantially all of the pixels in all three of the phase shifted images. A height map is generated as described above. The resulting Vector Length (the m of equation 1) map is used to detect pixels that have been under exposed, for example when the Vector Length is less than a threshold. The height value at those pixels is not well known because the signal to noise ratio (SNR) at those pixels is poor;

not enough light was returned in the phase shifted images to achieve a satisfactory SNR. A second set of constant exposure and illumination conditions, where the exposure is longer and/or the applied light level is higher, is then used during acquisition of a second group of three phase shifted images. A second height map is computed from this second group of images. Extension of the dynamic range is achieved by substituting heights from this second height map for those in the first height map at pixels where the Vector Length in the first height map were below the threshold. Thus the quality of this merged height map is improved because fewer, and possibly no, pixels will have Vector Lengths less than the threshold that signifies a poor SNR. The advantage of this approach over the first approach is that the exposure times and applied light levels used to acquire the first set of three images and the second set of three images need not be precisely known. It is sufficient that they are constant while the three phase shifted images of a single group are acquired and that the values of one group are different from those of the other by approximately two orders of magnitude.

Figure 9:
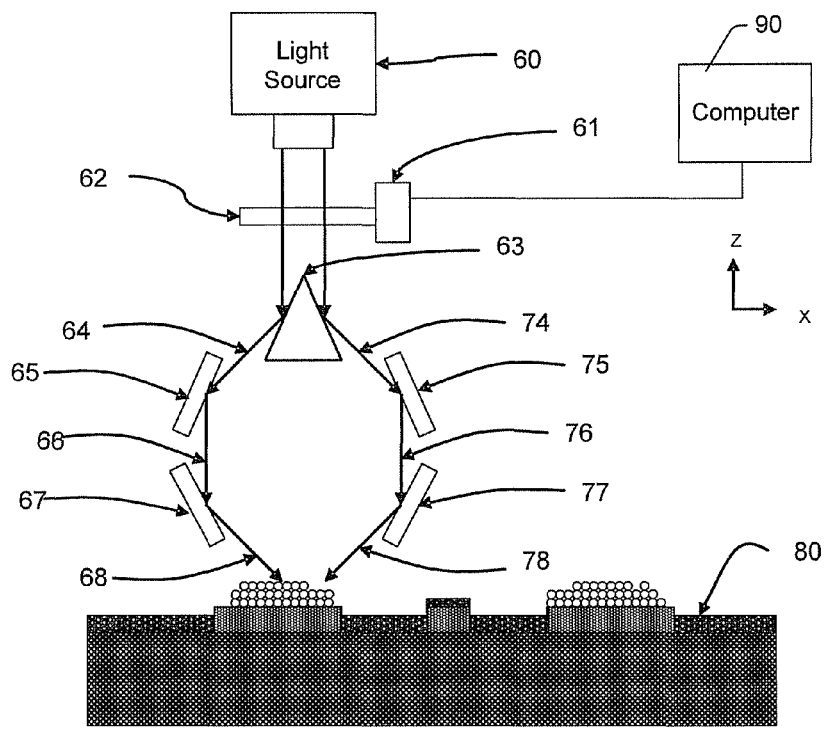
FIG. 9 is a simplified schematic side view illustrating a partially assembled circuit board and conceptually showing a pattern projector assembly.

In the embodiment of FIG. 9, light source 60 provides light to a light controller that includes LCD 62 under control of LCD controller 61 that is in turn controlled by a computer 90. In addition to providing a computer controllable modulation pattern, in this configuration, the light controller implemented by LCD 62 can select optical channel A, comprised of mirrors and 63, 65 and 67 or B, or optical channel B comprised of mirrors 63, 75 and 77, without any moving parts. In FIG. 9, optical channel A and B are configured to deliver light to the target surface with different illumination characteristics from each other; in this case they have different illumination azimuths. However, it is possible also that they could differ in their elevation angles, in their magnification in their depth of field, or in some other characteristics as will be clear to those skilled in the art.

Figure 10A:
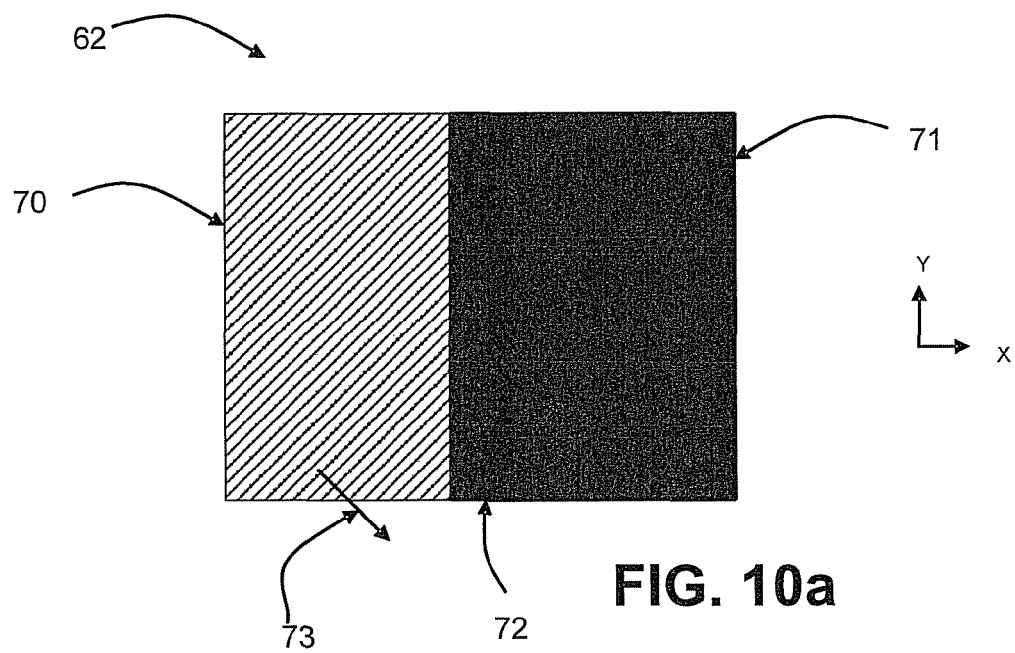
FIGS. 10-12 are top views schematically illustrating aspects of the light source of the pattern projector assembly shown in FIG. 9.

FIG. 10a is a top view of the LCD. The left side 70 is shown schematically with a pattern with direction 73 that will be projected onto the target surface through optical channel A. The right side 71 of the LCD is opaque and will therefore block substantially all light from entering optical channel B. Note that the opaque area comprises more than 50% of the size of the LCD, whose midpoint in the X direction is marked at 72.

Figure 11:
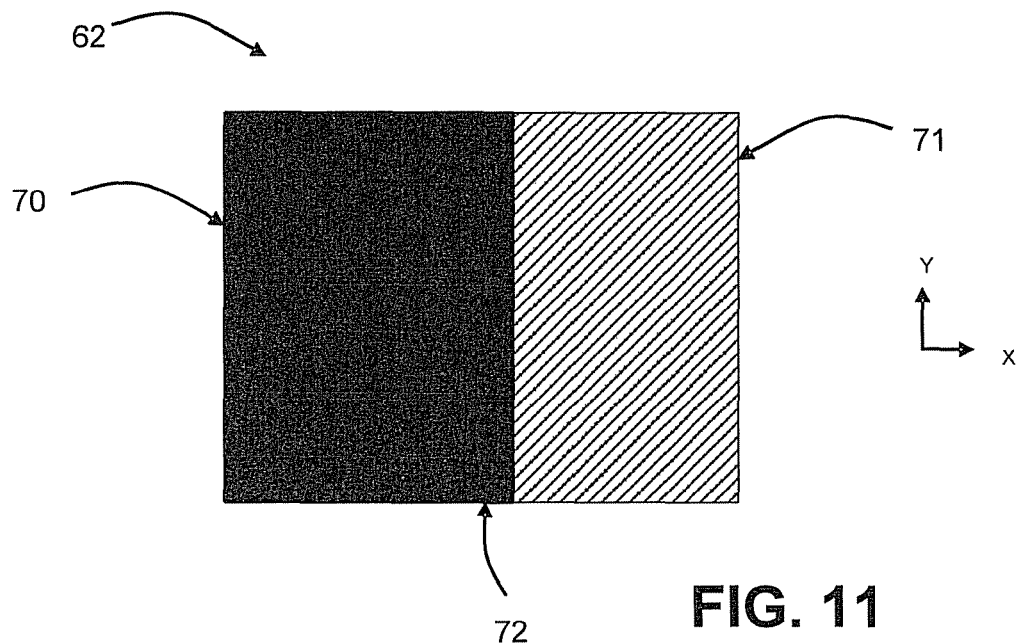

FIG. 11 schematically illustrates the condition of the LCD when optical channel A is disabled and optical channel B is used to project the light pattern onto the target surface. Again note that more than 50% of the LCD is opaque.

Figure 12:
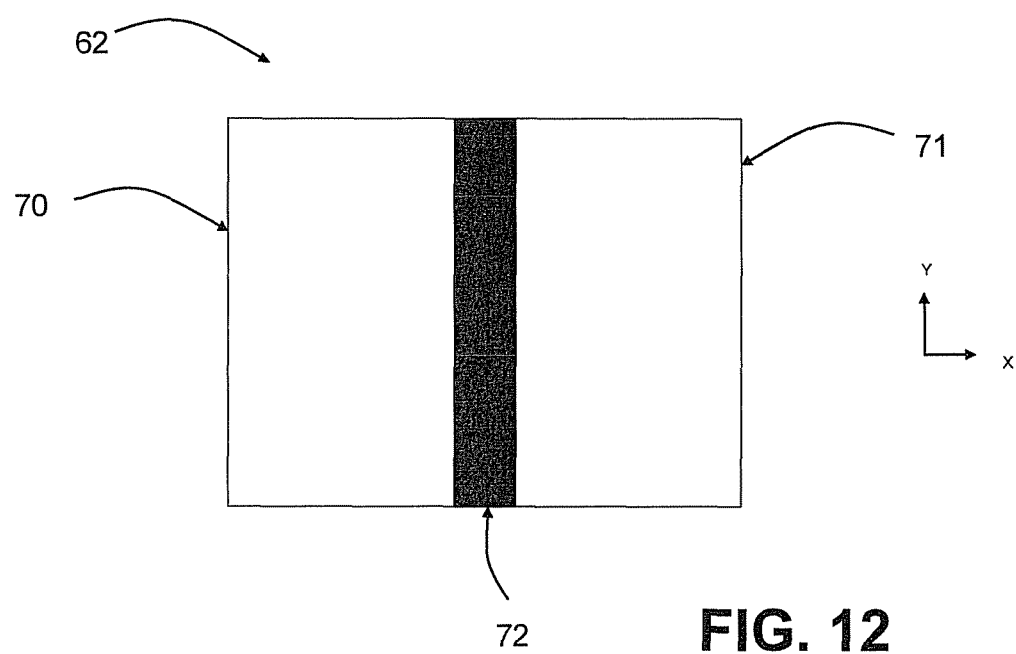

Referring to FIG. 12, the center zone 72 of the LCD must be opaque when the projection system is being used to deliver light either through channel A or channel B because the lens system (not shown) is preferably designed so that the focal plane is substantially co-located with the target surface 80 and therefore the optical pattern will not be in focus as it strikes dividing mirror 63.

As long as the LCD has enough pixels to form projection patterns with sufficient resolution onto the target through either channel A or B, then there is no loss of performance associated with discarding center zone 72.

For example, in various embodiments the pattern wavelength as projected onto the target surface for 3D solder paste inspection is approximately 250 µm; the pattern wavelength as projected onto the target surface for component 3D AOI inspection is approximately 25 mm; and the XY extent of the projected pattern onto the target surface for either application is 30 mm square.

Forming an approximation of a sine wave intensity modulated projection pattern requires at least two pixels per wave, but operating at or near this limit requires a high performance optical low pass filter to suppress harmonics. In exemplary embodiments, five pixels per wave length would be used to form the projected sine wave thereby requiring only a moderate performance optical low pass filter for harmonic suppression. Note that it is not necessary to suppress all harmonics in order to generate height maps of sufficient quality, especially if more than three images are acquired before height reconstruction. Thus, a projection system can use a LCD of lower resolution, or have a larger image projection pattern area or a mix, and still be used as part of a system able generate high fidelity height maps if more than three images are with more than three phase shifts are acquired.

In the configuration where five pixels per wavelength is used, for a projection pattern with a linear dimension equal 30 mm, a region of the LCD 120 wavelengths or 600 pixels is required.

Referring again to FIG. 10a, the left hand side 70 used to address optical channel A will be 600 pixels square for the configuration where five pixels per wavelength is used. Referring again to FIG. 11, the right hand side 71 used to address optical channel B will be 600 pixels square for the configuration where five pixels per wavelength is used.

Note that with an LCD of sufficient resolution, the concept of having two optical paths addressable by sections of the LCD can be extended to three or more paths. Dividing mirror 63 would need to have more than two illuminatable facets and additional sets of mirrors similar to 75 and 77 would need to be included.

Figure 13:
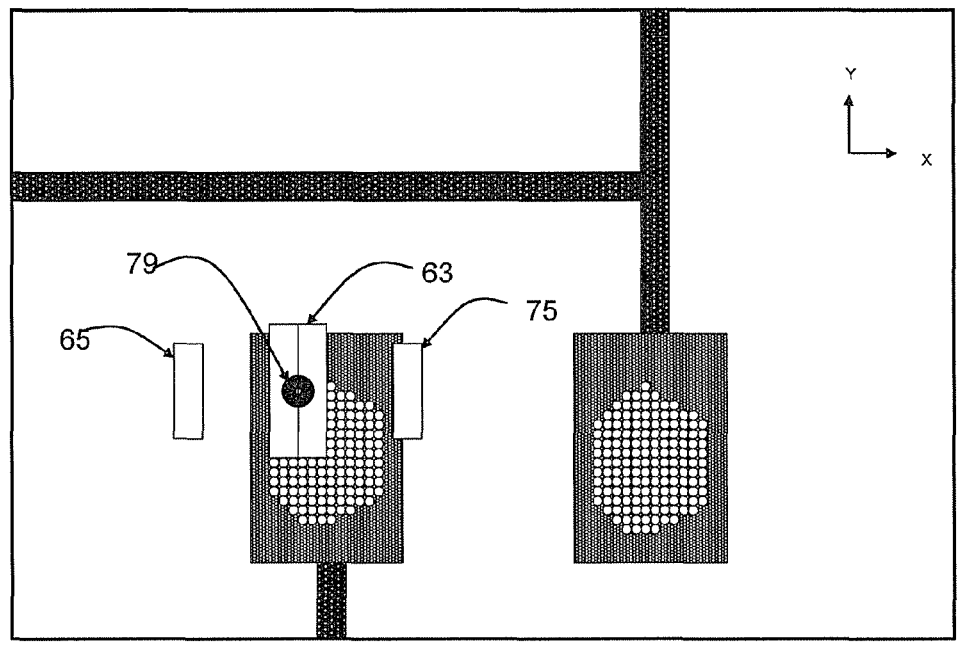
FIG. 13 is a partial top view of the pattern projector assembly illustrated in FIG. 9.

FIG. 13 is a partial top view of the pattern projector assembly illustrated as a side view in FIG. 9. In FIG. 13, the light source 60 and LCD 62 are not shown for clarity. Mirror 63 of FIG. 13 corresponds to the mirror 63 of FIG. 9. Similarly, mirrors 65 and 75 of FIG. 13 correspond to mirrors 65 and 75 of FIG. 9.

In certain implementations, the portions of the projection assembly illustrated in FIGS. 9 and 13 comprised of mirrors 63, 65, 67, 75 and 77 are made so that they can rotate about the Z axis centered on position 79 in order to allow the projection system to illuminate the target surface 80 from varying illumination azimuth angles. This rotation about the Z axis is under computer control and will preferably stop prior to and during multiple exposures of the target surface. It is envisioned that a system able to rotate as described may be comprised of only one optical channel.

Figure 10B:
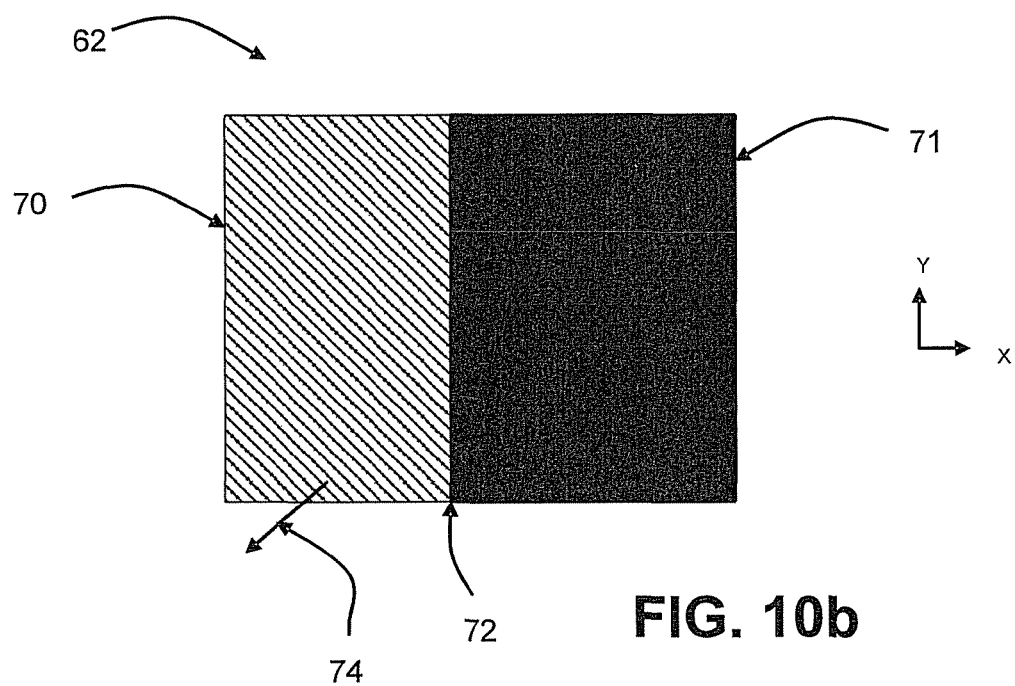

Referring to FIG. 10a, LCD 62, under control of a computer, has a wave pattern on its left hand side 70 with wave direction 73. Referring to FIG. 10b, the LCD 62, under control of a computer, has a wave pattern on its left hand side 70, where the wave direction 74 is has changed from that illustrated in FIG. 10a.

The ability of the computer to control the pattern of the LCD, in this example by rotating the wave direction, allows the system to keep the wave number direction optimized for the selected illumination azimuth angle.

There are two ways to rotate the pattern generator so as to provide optimal illumination to the rotating optical channels described above: In the first way, the LCD physically rotates about the Z axis in coordinated motion with the rotation of the optical channels. In the second way, the pattern and the blackout regions of the LCD rotate under control of the computer in coordinated motion with the rotation of the mirrors discussed above, while physically the LCD remains stationary. The second approach has the advantage of not requiring the LCD to physically rotate, but suffers from a loss of available pixel resolution when the rotated pattern is on a diagonal from the LCD edges.

Thus the light controller comprised of the transmissive LCD is able to vary the illumination characteristics delivered to the target using a single optical path and/or select a subset of available optical paths, each path having additional differing illumination characteristics.

Figure 15:
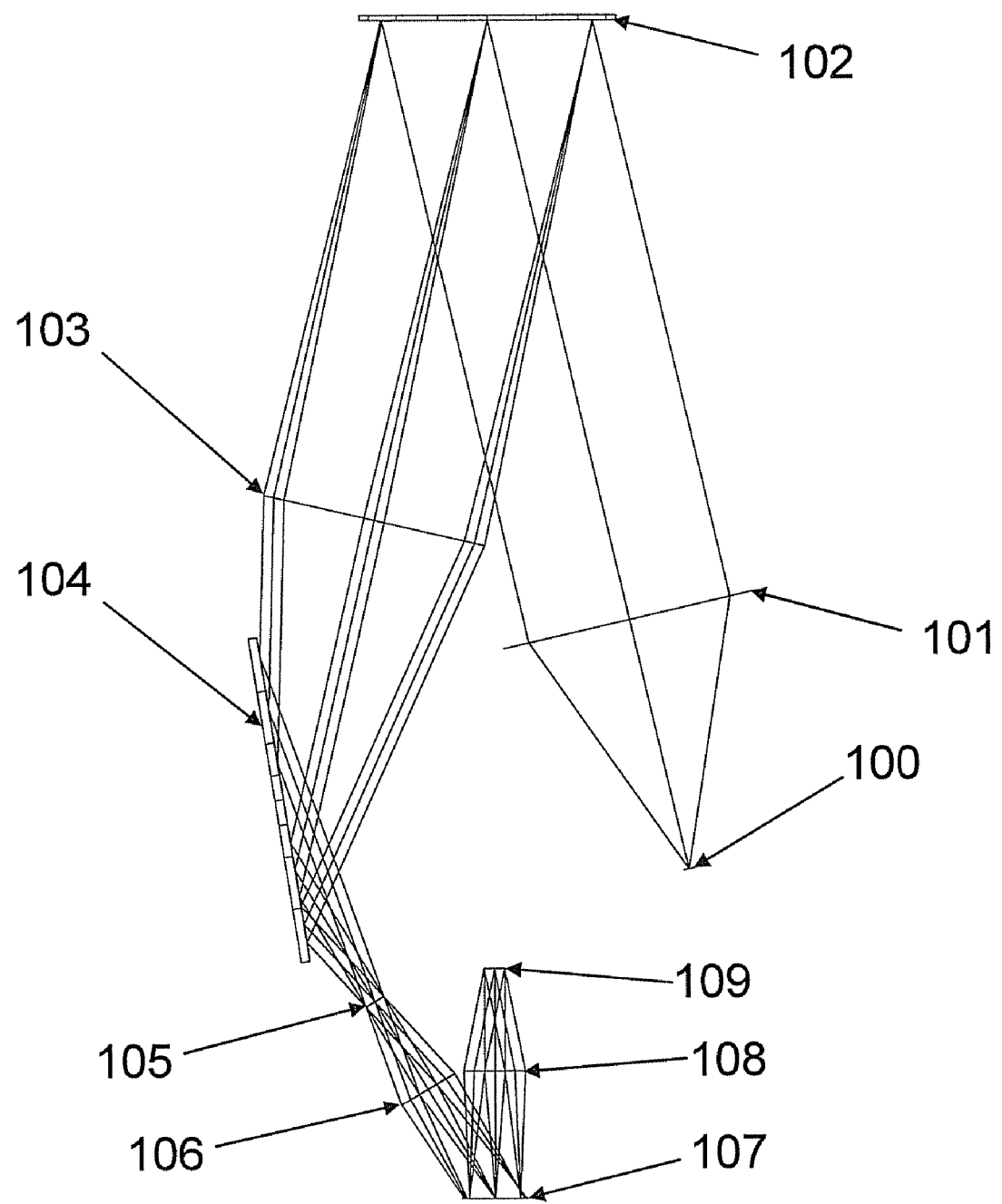
FIG. 15 is a side view of an illustrative optical system using a light controller comprised of a reflective spatial light modulator (e.g. LCoS or DMD) able to illuminate an area of the circuit board from a single distinct direction and adjust the pattern, where no macroscopically moving parts are required to adjust the pattern.

FIG. 15 is a side view of an illustrative optical system illustrating a light controller able to illuminate an area of the circuit board from a single distinct direction and adjust the pattern, where no macroscopically moving parts are required to adjust the pattern.

Light source 100 is a spatially localized light source such as an LED, Laser or the like. Lens 101 focuses the light onto light controller 102. (Other light sources, some not spatially localized can be used in place of light source 100 and lens 101 in other embodiments. Light controller 102 is, for example, a micro-mirror array (DMD) or a Liquid Crystal on Silicon array (LCoS) or the like able to, on a pixel by pixel basis controlled ultimately by a computer (not shown), reflect light or not into the subsequent optical path beginning with lens 103. Mirror 104 is used to direct the light towards the target surface 107 which, in exemplary embodiments is a circuit board, but which can be any surface to be inspected. Stop 105 and lens 106 are included to illustrate a type of projection system (telecentric) that offers the advantages of reduced magnification changes with variation in range. As discussed elsewhere herein, the system of this invention can work with or without telecentric optics. Lens 108 and imaging array 109 (such as a CCD or a CMOS array) are included for completeness and they schematically represent a camera system able to acquire images of the target surface 107.

As illustrated in FIG. 15, the reflective light controller 102 offers some advantages of the above-discussed transmissive light controller (LCD). These advantages relate to speed and light efficiency. LCD, DMD and LCoS devices are widely used in commodity television projection displays and are therefore relatively inexpensive, especially LCDs and DMDs. The DMD device is able change the pixel from "off" to "on" or vice versa (to rotate a micro-mirror from the one position to the other) in approximately 10 μs. The light efficiency of the DMD is very high, because the micro-mirrors introduce only very small light losses. The LCoS array is able to switch its pixel from "off" to "on" or vice versa in about 50 μs. The light efficiency of this type of reflector is much poorer, in large part because of the need to polarize the incoming light. State of the art transmissive LCD light modulators are able to switch pixels about as fast as an LCoS device, but these esoteric devices are expensive. Commodity transmissive LCD devices used in television projectors for example require approximately 5 msec to switch from 'off' to 'on' and vice versa. Also, transmissive LCD devices are not as light efficient as the micro-mirror arrays.

Figure 16:
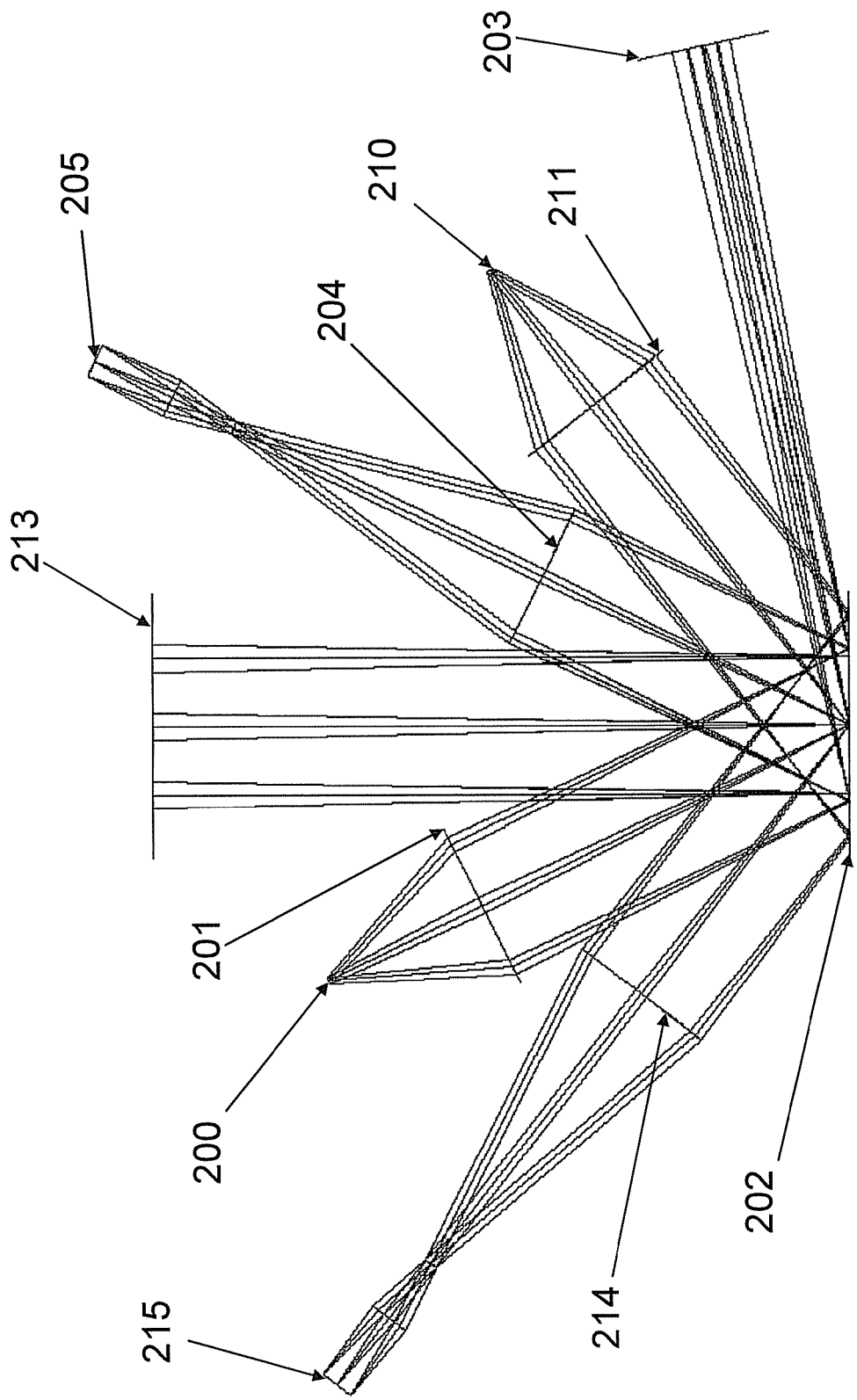
FIG. 16 is a side view of an illustrative optical system using a light controller comprised of a reflective spatial light modulator (DMD) able to select two distinct optical subsystems and to adjust the pattern, where no macroscopically moving parts are required to perform the selection or adjust the pattern.

To understand FIG. 16, it is important to realize that, for a DMD, the "off" condition of the micro-mirror does not absorb light; it directs the light to an angle where something in the optical system must keep it from reaching the target. In FIG. 16, light source 200 is a spatially localized light source that can be turned on and off in a short (~10 μs) time, such as an LED, a Laser or a strobe lamp or the like. Light from source 200 passes through lens 201 and reaches the light controller implemented here with a micro-mirror array 202. Micro-mirrors that are in the "off" angular condition for light coming from light source 200 will direct that light into light trap 203. Micro-mirrors that are in the "on" angular condition for light coming from light source 200 will direct that light into the optical channel beginning with lens 204 and ending at focal plane 205. So far in this discussion, the system of FIG. 16 is essentially the same as the illumination subsystem of FIG. 15, except that the mirror 104 of FIG. 15 used to direct the light onto the target is omitted from FIG. 16 for clarity. If mirrors like FIG. 15 mirror 104 were included in FIG. 16, then the two focal planes 205 and 215 could be made coincident and the illumination subsystems beginning with lenses 204 and 214 would deliver light to that single focal plane from two separate directions.

Continuing with FIG. 16, light from source 210 passes through lens 211 and reaches micro-mirror array 202. Micro-mirrors that are in the "off" angular condition for light coming from light source 210 will direct that light into light trap 213. Micro-mirrors that are in the "on" angular condition for light coming from light source 210 will direct that light into the optical channel beginning with lens 214 and ending at focal plane 215.

Still continuing with FIG. 16, only one light source, either 200 or 210, is energized at any one time. For example, if light source 200 is energized, the optical subsystem beginning with lens 204 and ending at focal plane 205 is selected for use. The light can be patterned or not, by toggling individual micro-mirrors of array 202 between their "on" and "off" states thereby directing portions of the light falling on array 202 between that optical subsystem and the light trap 203. The duty cycle of each pixel's "on" time is used to control the average intensity of light at that pixel delivered to focal plane 205 as per normal operation of a DMD based light modulator. It is via this duty cycle control of each pixel's average intensity that the pattern can be introduced to the projected light.

In FIG. 16, the "on" angular condition of a micro-mirror for one light source corresponds to the "off" angular condition of for the other.

It will be clear to those skilled in the art that FIG. 16 is schematic. Individual micro-mirrors that comprise micro-mirror array 202 can be in multiple angular states, only two of which have well controlled angle accuracy. These two states are what are referred to herein as "off" and "on". It will also be clear to those skilled in the art that the micro-mirrors will not instantaneously switch from one state to the other and that during the non-zero transit time from one state to the other light will be directed to angles between the angles that correspond to the two well controlled ("on" and "off" state) angles. For example, when source 200 is energized, light directed towards these intermediate angles will back-illuminate lens 211 and source 210. It is possible that a small portion of this back-illumination will scatter back onto mirror array 202 and thence into the optical subsystem beginning with lens 214. This is to be avoided because such back-scattered light may reach the target via the second optical sub system beginning with lens 214; this optical subsystem is intended to be used by light originating with source 210 only.

In FIG. 16, all optical elements are arranged in a single plane. It is possible to prevent back-scatter completely by deploying one set of the sources and subsequent optics out-of-plane. This way, the light swept between the intended optical subsystem and its light trap will neither directly enter nor back-illuminate another optical source or any of its components.

Even if the entire system is to be curtailed to one plane, those skilled in the art will recognize that it is possible to use baffles or other standard approaches to reduce the back-scatter effects.

Also, the amount of energy available for back-scattering is minimal because it is available only during the transit time. As mentioned above, the micro-mirrors can switch in approximately 10 μs. For most uses, the total exposure times will be on the order of milliseconds, so even with no counter measures and even under worst-case back-scattering conditions, only a small portion of total light delivered to the target will arrive through a deselected optical channel.

In this fashion, the system of FIG. 16, possibly extended in to three dimensions (out-of-plane) and possibly including back-scatter counter measures, is able to select between two optical subsystems by using one light source or the other and is able to generate patterned light through standard duty cycle intensity control without any macroscopically moving parts.

It will be clear to those skilled in the art that the system of FIG. 16 can be extended to more than two optical subsystems limited in practice only by the number of optical elements that can fit into the available space, keeping in mind the preference to avoid, during duty cycle intensity modulation, sweeping light through a deselected optical channel or optical elements that could scatter light into a deselected channel. For applications that require larger numeric apertures (NA), the maximum number of optical subsystems that can fit will be less than for those applications that are able to operate with a smaller NA.

If the optical system of FIG. 16 is implemented with an LCoS array at light controller location 202 rather than a micro-mirror array, then swept angles and back-scattering are not problematic because the pixel "off" condition is absorptive and the "on" condition is reflective. Therefore no sweeping of angles occurs in order to achieve intensity modulation. This permits an LCoS based system to make use of spaces that, in a micro-mirror based system, would preferably be reserved as 'keep out' areas in order to prevent light from entering deselected optical subsystems. However, LCoS systems require the incident light to be polarized and this introduces a substantial light loss. Additionally, LCoS arrays are substantially more costly than micro-mirror arrays. So, for the above reasons, systems requiring numerous independently addressable optical subsystems may be use light controllers preferably implemented with LCoS light modulators, whereas those with fewer independently addressable optical subsystems or with more stringent cost requirements or with more stringent light budgets may preferably be implemented with micro-mirror arrays.

It will be clear to those skilled in the art that, unlike the previously discussed light controller using a transmissive LCD, all of the resolution of the micro-mirror or LCoS arrays is used for each independently selectable optical subsystem.

Figure 17:
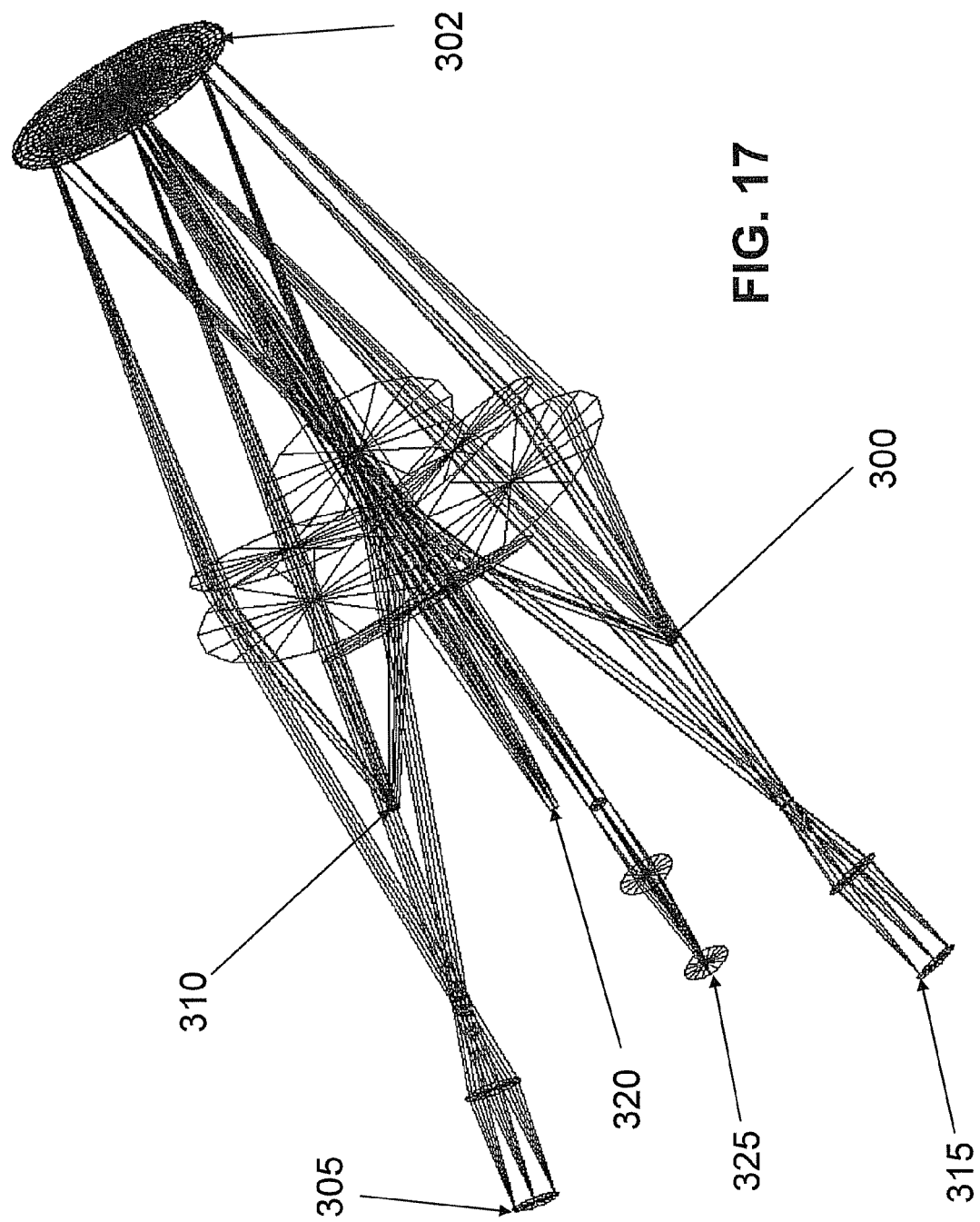
FIG. 17 is a perspective view of an illustrative optical system using a light controller comprised of a reflective spatial light modulator (e.g. LCoS or DMD) able to select three separate optical subsystems and to adjust the pattern, where no macroscopically moving parts are required to perform the selection or adjust the pattern.

FIG. 17 is a perspective view of an illustrative optical system using a light controller implemented with a reflective spatial light modulator 302 (e.g. LCoS or DMD). There are three separate illumination sources, 300, 310 and 320. As per the discussion related to FIG. 16, this system is able to select one optical subsystem ending in one of the three focal planes 305, 315 or 325 by energizing only one source at a time. Also per the discussion related to FIG. 16, it is also able to adjust the pattern, where no macroscopically moving parts are required to perform the selection or adjust the pattern. The mirrors that would direct the light from each of the three optical subsystems onto a single collocated focal plane (similar to the mirror 104 of FIG. 15) are omitted for clarity.

Therefore, the systems of FIGS. 16 and 17 use a reflective light controller where the light delivered to the light controller originates in first and/or second light sources and is incident on the light controller at first and/or second angles and where selection of a subset of available optical paths, each having differing illumination characteristics, is achieved by which light sources are energized.

It will be clear to those skilled in the art that there may be some occasions where energizing more than one illumination source concurrently may be advantageous. For example, if the pattern is removed from the light controller 302 and all three light sources 300, 310 and 320 are turned on at the same time, unpatterned light will arrive at the target from multiple source angles. Some illumination requirements can be furthered from this illumination condition. An example is illumination of a fiducial on a circuit board, which often is preferably illuminated with a system intended to approach "cloudy day" illumination, where at least some light comes from all angles.

In summary, for the systems described in FIGS. 16 and 17, selection of a given single angle of illumination is achieved by energizing one and only one illuminator. The pattern is introduced into the projected light by controlling the reflective duty cycle of the light controller (DMD or LCoS device), this in turn controlled by a computer (not shown). For phase profilometry, the computer will control the light controller so as to generate an intensity pattern that is preferably sinusoidal and of a given phase. Shifting the phase requires only that the computer command a different pattern. Selecting one of the three illustrated illumination angles requires only that the computer energize one and only one of the illuminators. It should be clear that more than three angles are possible, depending only on the ability to fit the required optics into the available space and that the available space grows as the NA of the optics decreases and vice versa.

Thus phase shifting and azimuth selection is done without macroscopically moving parts.

As discussed elsewhere, the capability of adjusting the illumination azimuth angle is not particularly advantageous for the inspection of solder paste. The benign situation with regards to solder paste does not apply once components have been added to the circuit board; components come in varying heights and are frequently placed closely to one another.

Under these conditions, embodiments are employed that are able to adjust the illumination azimuth angle to minimize or eliminate this shadow effect for conditions on a circuit board populated with components.

Also, such embodiments of the inspection system are able to automatically determine the optimal illumination azimuth angles. Automatically computing the optimal illumination azimuth angles can be accomplished from the nominal topography of the populated circuit board as follows:

Each component's nominal X, Y and Z dimensions are known from Machine Readable data. The source of this Machine Readable data can be the board design, or data extant with the mounters on the line, or some other source;

Using this Machine Readable data, a 3D map of the nominal populated circuit board is constructed;

The illumination elevation angle (angle of illumination above the horizon) of the system is known by virtue of its construction or a calibration step or a mix thereof;

A 3D modeling method is used to select one or more optimal illumination azimuth angles so all interesting features of or on the circuit board will be illuminated (not shadowed);

A 3D modeling method is used to select one or more optimal illumination azimuth angles so that the component leads, if they are not obscured by the component body itself (e.g. a BGA) will be illuminated (not shadowed);

The previous steps are preferably accomplished so as to satisfy the illumination requirements for the many parts that will typically be visible within a single field of view that is preferably 30 mm square. But, if there is no single illumination azimuth angle, or fixed set of angles, that satisfies the illumination requirements for all interesting features within that field of view, it may be necessary to rotate the illumination azimuths one or more times to acquire additional images of the field of view.

Figure 7:
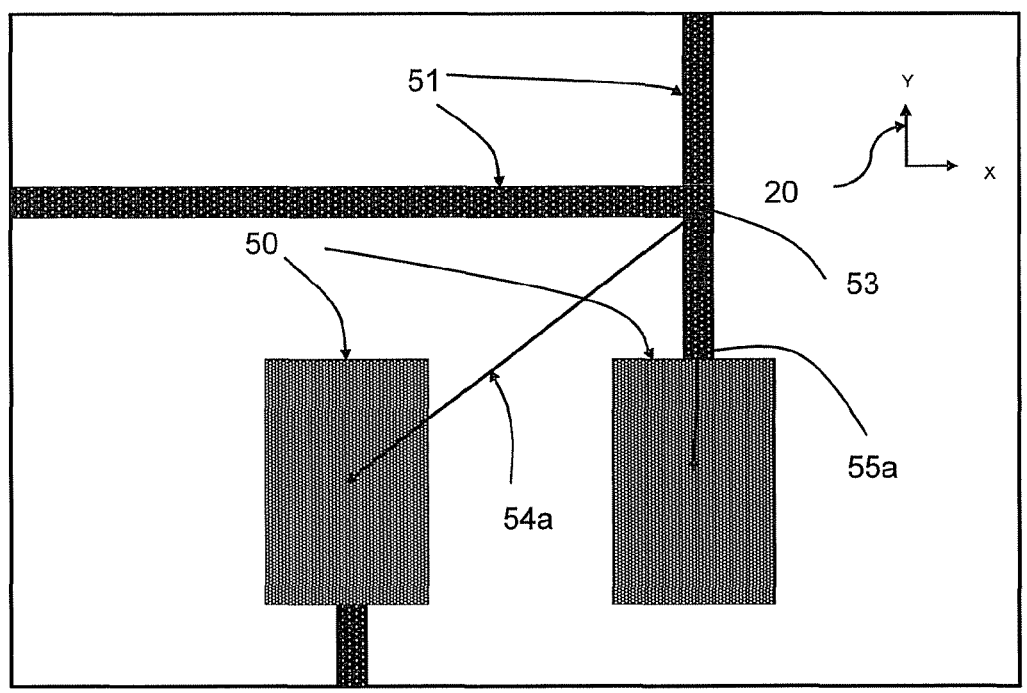
FIG. 7 is a schematic representation of a 2D image of a component land pattern prior to solder paste print.

FIG. 7 is a schematic representation of a 2D image of a component land pattern prior to solder paste print. 3D height maps and 2D color images can be used to characterize aspects of the circuit board, including the height, XY position, color and brightness of the land pattern 50 where solder contacts will later be formed. The X and Y positions of each of the pads 50 of the land pattern can be learned from these images relative to nearby features, such as circuit traces 51. Thus, later, when the land pattern 50 is covered with solder paste, a component, etc. and the circuit board is again scanned by the system of the present invention, the land pattern's position can be calculated from nearby features that will remain uncovered.

These reference features are preferably selected to be close enough to the land pattern to allow them and the land pattern to be viewed in a single optical image. The features are also preferably selected to be far enough away from the land pattern to ensure that they will not be covered by the solder paste or the component that will be added later. Furthermore, the features are preferably selected to have, in aggregate, high spatial frequencies in both the X and Y directions. This high spatial frequency means that the X and Y positions of those features can be unambiguously calculated.

Figure 8:
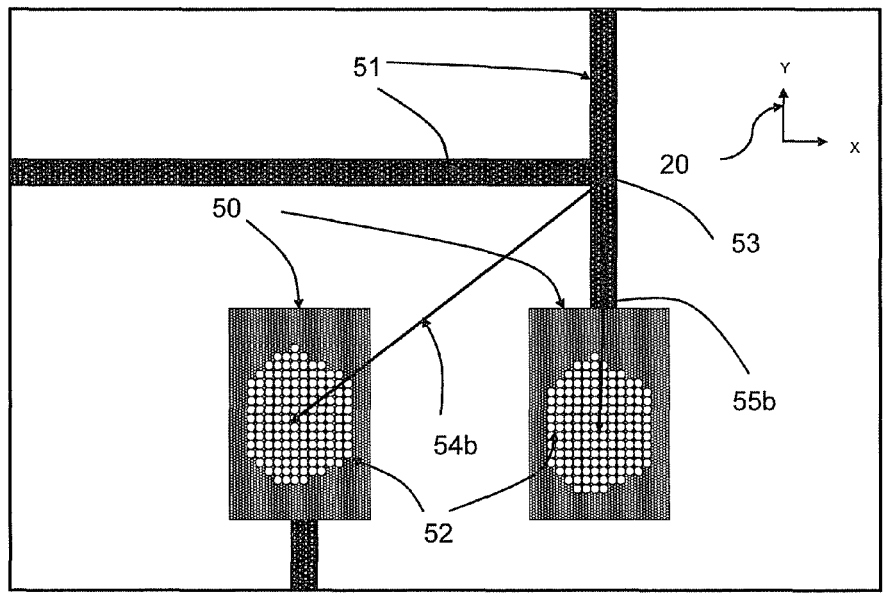
FIG. 8 is a schematic representation of a 2D image of a component land pattern after solder paste print.

Refer to FIG. 8, where the value add operation is solder paste printing and where 2D and 3D images are acquired after solder paste printing. Registration, the XY error of each solder paste deposit 52 from its corresponding pad 50, can be calculated even if the pad 50 is entirely covered with solder paste 52. This is done by comparing the calculated XY position of the solder paste deposit from the positions of the nearby reference features, for example, circuit traces 51. As described above, the contact pad 50 XY positions relative to the same features can have been learned prior to solder paste print.

Referring to FIG. 7, for each pad, a first set of vectors 54*a* and 55*a*, from the datum formed for example, by the junction 53 of circuit traces 51, to the center of each pad is calculated.

It is possible to learn the positions of the pads from CAD data. But, if CAD data is unavailable, a way to calculate the positions of the pad from imagery is according to the following procedure:

Acquire 2D and 3D images of the circuit board before solder paste print (Before Image)

Acquire 2D and 3D images of the same circuit board after solder paste print (After Image)

Normally, many images are required to cover the entire circuit board, so the following applies to Before and After images that have been acquired at substantially the same position on the circuit board;

Coarsely register the 2D After image to the 2D Before image based upon the XY position of the camera and the found position of the circuit board fiducial marks Precisely register the 2D After image to the 2D Before image based upon the images' content using, for example, normalized cross correlation.

Calculate the difference image, subtracting the Before image from the After image.

Use morphological operators, such as the erosion operator or the open operator, to remove high frequency noise from the difference image The blobs left over in this difference image are at the XY locations of the solder paste 52. The corresponding locations in the Before provide initial coordinates of the unprinted contact pads 50.

Learn the Independent Characteristics that describe the unprinted contact pads 50 from the content of the Before image near the initial coordinates In the Before image, segment each contact pad 50 that had solder paste deposited thereon, from the background using the Independent Characteristics of the contact pads In the Before image, compute the centroid of each solder contact pad 50.

Select one or more nearby datums that satisfy the conditions: having, in aggregate, high spatial frequencies in both the X and Y directions; and are not positioned on the circuit board so that they will later be covered by a component (note: This is not a requirement for solder paste registration measurement because components will not yet have been placed when solder paste registration inspection is performed. Rather, having datums that are not covered by components is preferred because they can be later reused to calculate the component placement position errors as well.); and are not so far from the contact pads as to be outside the field of view of the camera when the camera is positioned to acquire an image of the solder contact pads.

In the Before image, for each contact pad 50, compute a vector from the one or more nearby datums to the centroid of that contact pad.

Referring to FIG. 8, for each solder paste deposit, a second set of vectors 54*b* and 55*b* from the datum formed, for example, by the junction 53 of circuit traces 51 to the center of each solder paste deposit is calculated from the 2D and 3D images acquired after solder paste print. The center of each deposit can be calculated from its 2D or 3D centroids.

The difference between these two sets of vectors (54*a*-54*b* and 55*a*-55*b*) is a measure of the amplitude and direction of the registration error for each solder paste deposit 52 relative to its corresponding pad 50. The error measurement is thereby substantially independent of imprecision in the XY motion subsystem of the inspection device.

Therefore, having knowledge of the XY positions of the land pattern 50 prior to the value add operation of solder paste printing makes it possible for the inspection machine to have less precise and less expensive mechanical stages and still yield precise measurements of solder paste registration errors.

The junction of circuit trace 53, used to establish a nearby XY reference location, can be considered to be an Artificial Fiducial, in that it does not have the primary purpose of being located (as is the case with fiducial marks). Multiple Artificial Fiducials can be used to establish the XY positions of features on the circuit board with increased XY accuracy and reliability. When these are redundant the improved accuracy of XY position comes from a merging of multiple fiducial positions, for example using a least squares fit. Reliability is increased because the use of multiple Artificial Fiducials increases the probability that at least one such Artificial Fiducial will remain visible within a desired field of view and after various stages of circuit board assembly.

A similar arrangement works for the value add operation of component placement. Once the land pattern positions are known relative one or more Artificial Fiducials, it is possible to compute errors in the XY placement position of the component in the same way as for solder paste. Note that XY placement position should be understood to include rotation about the Z axis. This rotation error can result in a lateral (X or Y) displacement of individual pads of a device and becomes more significant as the device's size (in X or Y) becomes larger.

It is also possible to use a reference image to form vectors 54*a* and 54*b* from an instance of a circuit panel other than the one being inspected for solder paste or component position as long as the reference datum 53 and the pad 50 locations relative to that reference datum are unchanged.

Despite the above, measurements of solder paste registration and XY component position remain dependent upon the optical characteristics, for example, distortion, of the camera's optical system.

The camera's optical system can be manufactured so that these characteristics are acceptably small, or so that they can be measured and calibrated to enable software to remove their effects. One optical characteristic that is particularly important in this application is telecentricity. To the extent the receive camera optics are non-telecentric, variations in range to the target surface manifest themselves as changes in magnification. Thus, the vector lengths from which, for example, solder paste registration errors can be calculated, will be increasingly overestimated as the target surface is less distant from the camera.

The system of the present invention can use telecentric optics to suppress this effect, or it can correct for this effect by:
Measure the absolute range to the target by using the computer and LCD to generate a suitable pattern for projection onto the target of unknown range. This pattern can be a spot, or an array of spots, or some non-repetitive pattern that therefore not be susceptible to phase wrapping. It can also be a repetitive pattern where the wrap height is much greater than the physically possible range of height values, so that a wrap cannot occur.
Once the target range is known, if the non-telecentric optics are suitably characterized in the factory, the effects of variable magnification that is dependent upon range can be removed.

A non-telecentric optical system offers the advantage of lower cost and bulk at the expense of extra compute, measurement and calibration requirements.

Measurement of solder paste metrics, or component placement metrics is but one step in determining whether an assembly is acceptable or not. Thresholds or acceptability or tolerances must be applied to these measurements. Measured parameters that fall outside the relevant range, or possibly ranges, of acceptability indicate a possible defect. The inspection system of this invention is able to perform this threshold or tolerance test and indicate, through a user interface or through a machine to machine interface, that the circuit board under inspection has a possible defect.

Figure 14:
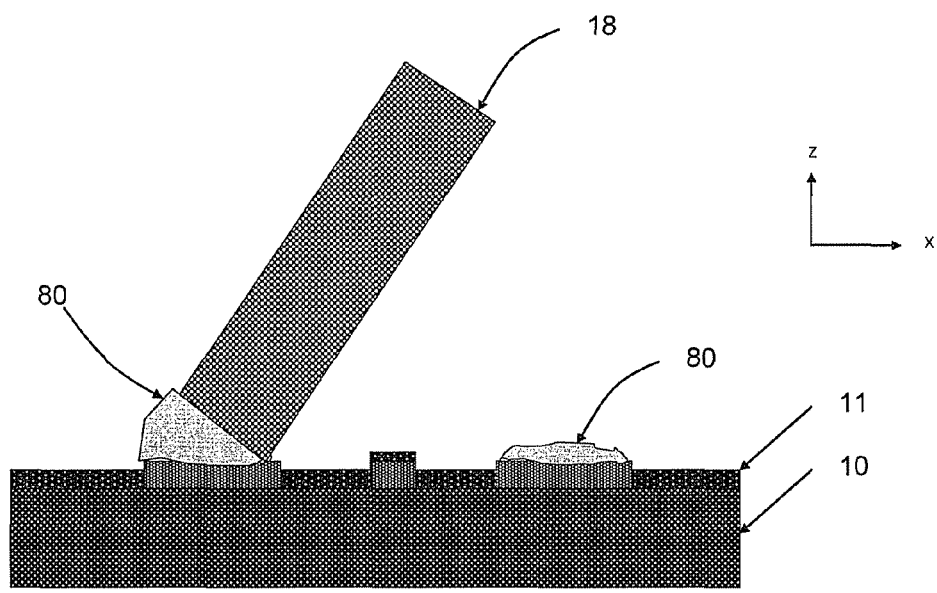
FIG. 14 is a simplified schematic side view illustrating a partially assembled circuit board with a "tombstone" error.

In addition to detecting defects, the measurements can be used determine the defect category. For example, the Machine Readable data contains nominal component dimensions (XY and Z) and nominal component placement positions. Therefore, if the component is missing entirely, it will be substantially true that no height will be present in the immediate vicinity of the nominal placement position of the component, and the defect category, in this case "missing component" can be determined. Because the vast majority of components are not cubes, it is also possible to discern tombstone (see FIG. 14) or billboard (not illustrated) from other error categories or from proper placements. The ability to perform the function of determining error categories, herein referred to as automatic Error Categorization, is very useful to SMT operators. When Machine Readable data is available, the system of the present invention is able to perform automatic Error Categorization without needing to be trained with visual examples of each error type.

Additionally, information about the circuit board, including for example the above mentioned measurements, whether an error was detected, its Error Category, etc. can be recorded to a data base associated with circuit board unique identification, if such is available. Well known Statistical Process Control (SPC) techniques can be applied to this recorded data thereby allow the inspection system to generate warnings and errors in more ways than can be accomplished by the use of simple error and warning thresholds alone.

AOI, especially when deployed after reflow, is used to screen assemblies for errors. When an error is found, it can be repaired. However, while they can be very detailed, images acquired post-reflow often do not reveal the cause of the error. An example of a frequently occurring error type is a tombstone part 18 illustrated in FIG. 14. A tombstone error can occur because an incorrect amount of solder paste was deposited, or because the component 18 was positioned incorrectly as it was placed by the mounter, or because there is oxidation on one of the leads (electro-mechanical contacts), or for other reasons.

Discovering the actual cause of the error from the many possible causes is important because it leads directly to corrective action. Discovering what is not the cause of the problem is also important, because ruling out one or more possible causes makes the process of fixing the problem simpler. Correcting or fixing the cause of the problem leads to fewer errors being made which provides a substantial financial benefit to the operators of SMT equipment.

Because the inspection system of this invention is be able to view the circuit board as it goes through various assembly steps, it is able to assist in this process of error diagnosis.
It does so by:
Keeping track of individual circuit boards by virtue of reading their bar code, or by some other unique identifying mark on the circuit board;
If no unique identifying mark is available, then it is possible to keep track of the circuit board by the use of sequence numbers, or numbers that are assigned to the circuit board by virtue of their sequence through the inspection system;
By saving all images acquired at the various assembly steps and keeping them associated with the unique identifying mark or sequence number, for example, by the use of a relational or object data base;
Saving all measurements, error determinations and error classifications derived from images acquired at the various assembly steps and keeping them associated with the unique identifying mark or sequence number, for example, by the use of a relational or object data base;
Providing an easy to use interface so that when an error is found by computer processing of images, or when a user indicates interest in a certain area, all images and data related to that area are fetched and presented to the user.

In order to make meaningful measurements of a circuit board, the system of this invention must first locate the position of the circuit board. This is done by locating, or measuring the XY position of fiducial marks. Fiducial marks are designed onto the bare circuit board with the express goal of allowing them to be so located. Classically, this is done by acquiring a 2D image of a region, illuminated with user programmable non-structured light, in which the fiducial mark should be present. Standard image processing techniques locate the fiducial mark within that 2D image.

The system of this invention performs this fiducial locating operation in this standard way.

Both the 2D and 3D imaging systems of this invention can be used to acquire images that will not necessarily be used to distinguish good circuit boards from defective ones. Some 2D or 3D aspects of the circuit board may be interesting to the operator, possibly in ways that he has not envisioned at the time the circuit board was scanned.

Therefore, 2D images from the 2D color camera and 3D images generated by phase profilometry of scenes are acquired, recorded and possibly associated, using a data base, with the circuit board under inspection.

These preferably high resolution images can assist the user in viewing the circuit board. The resolution of the 2D color image is envisioned to be fine enough, with pixels size preferably 10-15 μm, to allow for significant user controlled "digital" magnification so that even the smallest components can be clearly seen.

Illumination for the 2D images can come from an illumination subsystem such as one comprised of an array of white LEDs. Ideally, this illuminator is able to fill $2\pi$ steradian. Most such illuminators are unable to achieve this ideal, but many come close. It is preferred that such a 2D illuminator can independently control the mix of specular (light that is sourced from a direction substantially parallel and coincident with the chief ray of the observation camera) and light coming from other directions, sometimes called diffuse light or low angle light. Such illuminators are commonly deployed within mounters and other SMT machines, because nearly all modern SMT machines must locate the position of the circuit board within their own local coordinate system. They do this by locating fiducial marks situated on the circuit board for this express purpose. This type of illuminator is optimized for generation of high quality 2D images and not for construction of height maps. The 2D images are commonly used for locating the XY positions of fiducial marks, making XY measurements of positions (XY and rotation about Z) of components, performing automatic character recognition of writing that may appear on the tops of components, recognizing the presence and positions of polarity marks, reading barcodes, etc. The system of the present invention implements this sort of 2D illuminator so that high quality color images of various targets of interest can be generated. These high quality color images are used for human viewing and also so that Independent Characteristics derived from them can be used in conjunction with Independent Characteristics from 3D images.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A manufacturing method including illuminating a target, comprising:
   providing a light controller including a light modulator having a plurality of pixels;
   projecting light from a first light source to the light modulator, wherein the light from the first light source is incident on the light modulator at a first angle;
   providing first and second optical paths between the light modulator and the target, wherein the first and second optical paths project at different angles;
   controlling the pixels of the light modulator to establish illumination characteristics for the first optical path and the second optical path.

2. The method of claim 1, further comprising:
   projecting light from a second light source to the light modulator, wherein the light from the second light source is incident on the light modulator at a second angle.

3. The method of claim 2, further comprising:
   establishing a third optical path between the light modulator and the target;
   projecting light from a third light source to the light modulator, wherein the light from the third light source is incident on the light modulator at a third angle; and
   controlling the pixels to establish illumination characteristics for the third optical path.

4. The method of claim 2, wherein controlling the pixels includes reflecting light from the light source.

5. The method of claim 2, wherein controlling the pixels includes patterning the light from the light source.

6. The method of claim 2, further comprising controlling the first and second light sources to selectively deliver light to the target via the first and second optical paths.

7. The method of claim 2, wherein the pixels of the light modulator have on and off states, and wherein controlling the pixels includes controlling a duty cycle of the on state.

8. The method of claim 1, wherein providing the first and second optical paths includes controlling the pixels.

9. The method of claim 1, wherein controlling the pixels to establish illumination characteristics includes:
   controlling the pixels to establish first illumination characteristics for the first optical path and; and
   controlling the pixels to establish second illumination characteristics for the second optical path.

10. The method of claim 1, wherein the illumination characteristics are selected from a group comprising:
    phase;
    wavelength;
    wave direction;
    illumination azimuth angle;
    illumination elevation angle;
    magnification;
    depth of field; and
    non-repetitive pattern.

11. The method of claim 1, wherein controlling the pixels includes controlling transparency of the pixels.

12. The method of claim 1, wherein controlling the pixels includes patterning the light from the light source.

13. The method of claim 1, wherein the target is a surface of a part, and wherein the method further comprises assembling the part into a final assembly.

14. The method of claim 13, wherein the part is an electronic component, and wherein the method further comprises mounting the electronic component on a circuit board.

15. The method of claim 1, wherein the pixels of the light modulator are controlled such that light from the first light source is deliverable to the target via the first and second optical paths.

16. An inspection system, comprising:
    a light controller including a light modulator having a plurality of pixels;
    a first light source arranged to project light incident on the light modulator at a first angle;
    wherein the light controller is operable to control the pixels of the light modulator to establish illumination characteristics for first and second optical paths between the light controller and a target, wherein the first and second optical paths project at different angles.

17. The inspection system of claim 16, wherein the light modulator is a transmissive LCD operable to establish the first and second optical paths.

18. The inspection system of claim 16, wherein the light controller is operable to control the pixels to establish respective first and second illumination characteristics for the first and second optical paths.

19. The inspection system of claim 16, further comprising a second light source arranged to project light incident on the light modulator at a second angle.

20. The inspection system of claim 19 wherein the light modulator is a micro-mirror array having the pixels controlled to establish the illumination characteristics for the first and second optical paths.

21. The inspection system of claim 19, wherein the light modulator is a liquid crystal on silicon array having the pixels controlled to establish the illumination characteristics for the first and second optical paths.

22. The inspection system of claim 19, comprising a third light source arranged to project light incident on the light modulator at a third angle, and wherein the light controller is operable to control the pixels of the light modulator to establish third illumination characteristics for a third optical path.

* * * * *